(12) United States Patent
Haider et al.

(10) Patent No.: US 11,564,745 B2
(45) Date of Patent: **\*Jan. 31, 2023**

(54) METHOD AND APPARATUS FOR COMPUTER AIDED SURGERY

(71) Applicant: Board of Regents of the University of Nebraska, Lincoln, NE (US)

(72) Inventors: Hani Haider, Carter Lake, IA (US); Osvaldo Andres Barrera, Omaha, NE (US)

(73) Assignee: Board of Regents of the University of Nebraska, Lincoln, NE (US)

( \* ) Notice: Subject to any disclaimer, the term of this patent is extended or adjusted under 35 U.S.C. 154(b) by 0 days.

This patent is subject to a terminal disclaimer.

(21) Appl. No.: 17/399,969

(22) Filed: Aug. 11, 2021

(65) Prior Publication Data

US 2021/0369349 A1 Dec. 2, 2021

Related U.S. Application Data

(63) Continuation of application No. 14/831,691, filed on Aug. 20, 2015, now Pat. No. 11,116,574, which is a
(Continued)

(51) Int. Cl.
*A61B 34/10* (2016.01)
*A61B 17/14* (2006.01)
(Continued)

(52) U.S. Cl.
CPC ............ *A61B 34/10* (2016.02); *A61B 17/142* (2016.11); *A61B 17/15* (2013.01); *A61B 17/154* (2013.01); *A61B 17/1675* (2013.01); *A61B 17/1703* (2013.01); *A61B 17/1764* (2013.01); *A61B 34/20* (2016.02); *A61B 34/30* (2016.02); *A61B 90/11* (2016.02); *A61B 90/36* (2016.02); *A61B 17/1626* (2013.01); *A61B 34/25* (2016.02); *A61B 90/90* (2016.02); *A61B 2017/00026* (2013.01); *A61B 2017/00199* (2013.01); *A61B 2017/00212* (2013.01); *A61B 2017/00221* (2013.01); *A61B 2017/00725* (2013.01); *A61B 2017/320052* (2013.01); *A61B 2034/101* (2016.02); *A61B 2034/102* (2016.02); *A61B 2034/104* (2016.02); *A61B 2034/105* (2016.02); *A61B 2034/107* (2016.02); *A61B 2034/108* (2016.02); *A61B 2034/2055* (2016.02); *A61B 2034/2068* (2016.02); *A61B 2034/2072* (2016.02); *A61B 2034/254* (2016.02); *A61B 2034/256* (2016.02); *A61B 2034/258* (2016.02); *A61B 2090/061* (2016.02); *A61B 2090/065* (2016.02); *A61B 2090/0812* (2016.02);
(Continued)

(58) Field of Classification Search
CPC ............................... A61B 34/10; A61B 34/20
See application file for complete search history.

*Primary Examiner* — Rochelle D Turchen
(74) *Attorney, Agent, or Firm* — Nasr Patent Law LLC; Faisal K. Abou-Nasr

(57) ABSTRACT

A number of improvements are provided relating to computer aided surgery. The improvement relates to both the methods used during computer aided surgery and the devices used during such procedures. Some of the improvement relate to controlling the selection of which data to display during a procedure and/or how the data is displayed to aid the surgeon. Other improvements relate to the structure of the tools used during a procedure and how the tools can be controlled automatically to improve the efficiency of the procedure. Still other improvements relate to methods of providing feedback during a procedure to improve either the efficiency or quality, or both, for a procedure.

20 Claims, 11 Drawing Sheets

Related U.S. Application Data continuation of application No. 11/927,429, filed on Oct. 29, 2007, now abandoned, which is a continuation-in-part of application No. 11/764,505, filed on Jun. 18, 2007, now Pat. No. 8,560,047.

(60) Provisional application No. 60/827,877, filed on Oct. 2, 2006, provisional application No. 60/814,370, filed on Jun. 16, 2006.

(51) Int. Cl.
| | |
|---|---|
| *A61B 90/00* | (2016.01) |
| *A61B 34/20* | (2016.01) |
| *A61B 34/30* | (2016.01) |
| *A61B 90/11* | (2016.01) |
| *A61B 17/15* | (2006.01) |
| *A61B 17/16* | (2006.01) |
| *A61B 17/17* | (2006.01) |
| *A61B 34/00* | (2016.01) |
| *A61B 90/90* | (2016.01) |
| *A61B 17/00* | (2006.01) |
| *A61B 17/32* | (2006.01) |
| *A61F 2/46* | (2006.01) |

(52) U.S. Cl.
CPC ... *A61B 2090/365* (2016.02); *A61B 2090/367* (2016.02); *A61B 2090/372* (2016.02); *A61B 2090/395* (2016.02); *A61B 2090/3937* (2016.02); *A61F 2002/4632* (2013.01); *A61F 2002/4633* (2013.01)

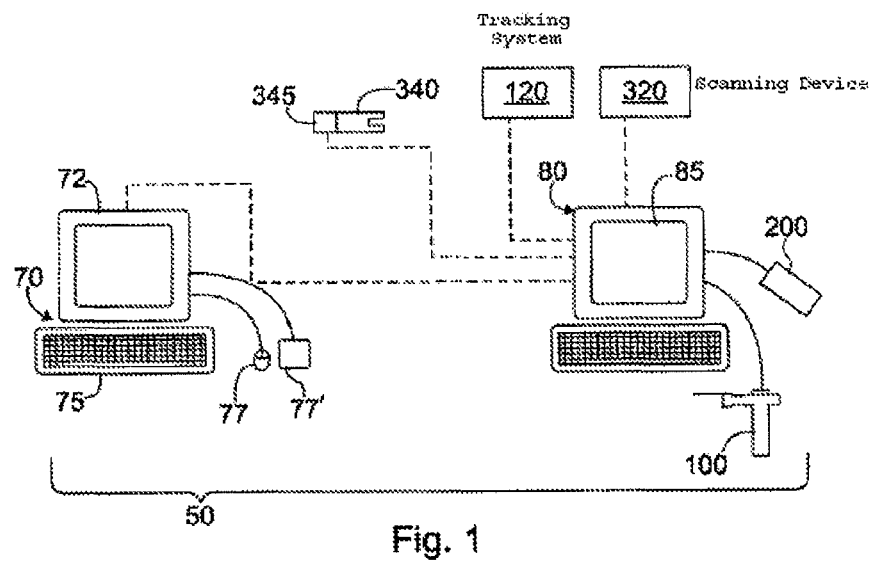
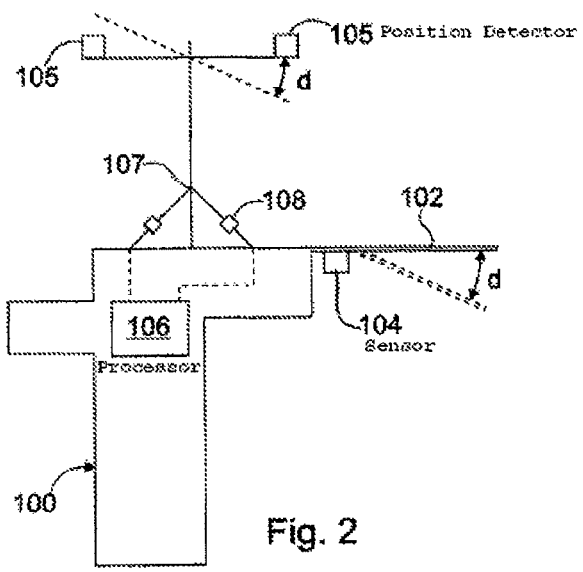

METHOD AND APPARATUS FOR COMPUTER AIDED SURGERY

CROSS REFERENCE TO RELATED APPLICATIONS

This application is a continuation of U.S. patent application Ser. No. 14/831,691, filed Aug. 20, 2015, titled "Method and Apparatus for Computer Aided Surgery", which is a continuation of U.S. patent application Ser. No. 11/927,429, filed Oct. 29, 2007, titled "Method and Apparatus for Computer Aided Surgery", Publication No. US-2008-0077158-A1, which is a continuation-in-part of U.S. patent application Ser. No. 11/764,505, filed Jun. 18, 2007, titled "Method and Apparatus for Computer Aided Surgery", now U.S. Pat. No. 8,560,047, which application claims priority from U.S. Provisional Application No. 60/814,370, filed Jun. 16, 2006, titled "Method and Apparatus for Computer Aided Orthopaedic Surgery", and U.S. Provisional Application No. 60/827,877, filed Oct. 2, 2006, titled "Method and Apparatus for Computer Aided Surgery". Each of the foregoing applications is hereby incorporated herein by reference in its entirety.

FIELD OF THE INVENTION

The present invention relates to the field of computer assisted surgery. Specifically, the present invention relates to various aspects of a surgical suite in which a computer provides guidance or assistance during a surgical procedure.

BACKGROUND

Many surgical procedures are complex procedures requiring numerous alignment jigs and intricate soft tissue procedures. Preparing and placing the alignment jigs and other preparation is often a significant part of the procedure. For instance, when performing a total knee replacement procedure ("TKR"), the prosthesis must be accurately implanted to ensure that the joint surfaces are properly aligned. If the alignment is inaccurate, the misalignment will lead to failure of the joint, requiring the complex task of replacing one or more portions of the knee prothesis.

To ensure that the prosthesis is accurately implanted, during a TKR procedure, the surgeon uses a variety of jigs to guide the cutting of the femur and the tibia. The jigs are complex devices that require significant time to install on the patient during the surgical procedure.

The advent of computer assisted surgery provides the promise of simplifying many of the complexities of surgical procedures. In some instances, the computer may be used to guide the surgeon during the process. Although computer assisted surgery holds promise, there are numerous aspects to be addressed to make a system commercially viable. For instance, in addition to improving the efficiency of the procedures, the quality of the resulting procedures should be addressed. Accordingly, there continues to exist numerous aspects of computer assisted surgery that require improvement to improve the efficiency and/or quality of the procedure. The end result will encourage medical professionals to migrate toward computer assisted surgical systems.

SUMMARY OF THE INVENTION

In light of the foregoing, a computer assisted surgical suite having a number of improvements is provided. For instance, a surgical suite having a computer and a surgical tool that communicates with the computer may be provided. The system also includes a tracking element for tracking the position of the surgical tool. In one aspect, the system allows the surgeon to perform a surgical procedure on a virtual model of the patient using the surgical tool. As the surgeon performs the procedure on the virtual model, the computer stores the information regarding the sequence of the steps performed and the position of the surgical tool during the procedure. Once the surgeon is satisfied with the results on the virtual model, the stored information can be used during the procedure to assist or guide the surgeon.

According to a further aspect, the computer controls operation of the surgical tool in response to information detected regarding the surgical tool. For instance, the system may track the position of the surgical tool relative to the patient. Based on the data regarding the position of the surgical tool, the computer may send signals to the surgical tool to control the operation of the surgical tool, such as reducing the speed on the tool or turning the tool on or off.

According to another aspect, the system provides a communication link between the surgical tool and the computer system that allows the surgical tool to control operation of the computer system and the computer system to control operation of the surgical tool.

Another aspect of the system is directed toward the use of the surgical tool in a free hand procedure to reduce or eliminate the use of jigs during a procedure. In such a procedure, the computer tracks the position of the surgical tool relative to the patient and displays the results on a screen to guide the surgeon in the procedure. In a resection procedure, the system may be configured to identify the patient tissue with different colors to identify the proximity of the tissue to the resection boundaries. For instance, tissue that is not to be resected may be illustrated in a red color, so that the surgeon can easily see that the tissue is not to be resected. Tissue that is to be resected may be illustrated in a green color. Further, tissue at the boundary of the portion to be resected may be illustrated in yellow, so that the surgeon can easily see that the cuts are getting close to the boundary.

Yet another aspect of the system is directed toward improving the display of information during a surgical procedure. Specifically, depending on which portion of a procedure is being performed, the surgeon may desire to change the view of the information being displayed. It can be cumbersome to change the view in the middle of a procedure to a different view. Accordingly, the system can be used to automatically switch to a particular view based on the position of the surgical tool. Additionally, the surgeon may program this information before a procedure, or the system can learn to recognize that a particular surgeon desires a particular view based on inputs from the surgeon during various procedures.

According to a further aspect, the system provides a method for assessing and improving the quality of a bone cut. For instance, the system measures various parameters relating to the quality of a bone cut, such as surface roughness, accuracy of each cut. If the parameter fall within pre-defined limits, the system indicates to the surgeon that the resection was successful, so that the prosthesis can be implanted. If one or more parameter falls outside the pre-defined limits, the system may calculate the step or steps necessary to correct the bone cuts so that the surgeon can perform the necessary correction.

Another aspect of the invention is directed improving the monitoring of the surgical tool. For instance, in certain aspects of computer assisted surgery, the position of certain surgical tools may be quite important in assessing the steps necessary during the procedure. However, during the procedure, operation of the surgical tool may cause the tool to deflect. The deflection may result in the system misidentifying the actual position of the surgical tool. Accordingly, the present system may include one or more sensors for detecting deflection of a portion of the surgical tool and an element for modifying the tracking element in response to the detected deflection.

A still further aspect of the present invention is directed to a marker that is used for marking tissue to be resected. The marker includes an actuator that responds to signals from the computer system. A tracking element provides data to the computer regarding the position of the marker. Based on the position of the marker, the computer controls the marker between an extended position and a retracted position. Specifically, if the computer detects that the marker is on a portion of the patient that is to be marked, then the computer controls the marker to extend the marker to the extended position so that a tip of the marker is exposed to mark the patient. Alternatively, if the marker is on a portion of the patient that is not to be marked, the computer controls the marker to retract the tip of the marker so that the marker cannot mark the patient.

DESCRIPTION OF THE DRAWINGS

The foregoing summary and the following detailed description of the preferred embodiments of the present invention will be best understood when read in conjunction with the appended drawings, in which:

FIG. 1 is a diagrammatic view of a computer assisted surgical suite.

FIG. 2 is a diagrammatic view of a surgical tool of the surgical suite of FIG. 1.

DETAILED DESCRIPTION OF THE INVENTION

Figure 3:
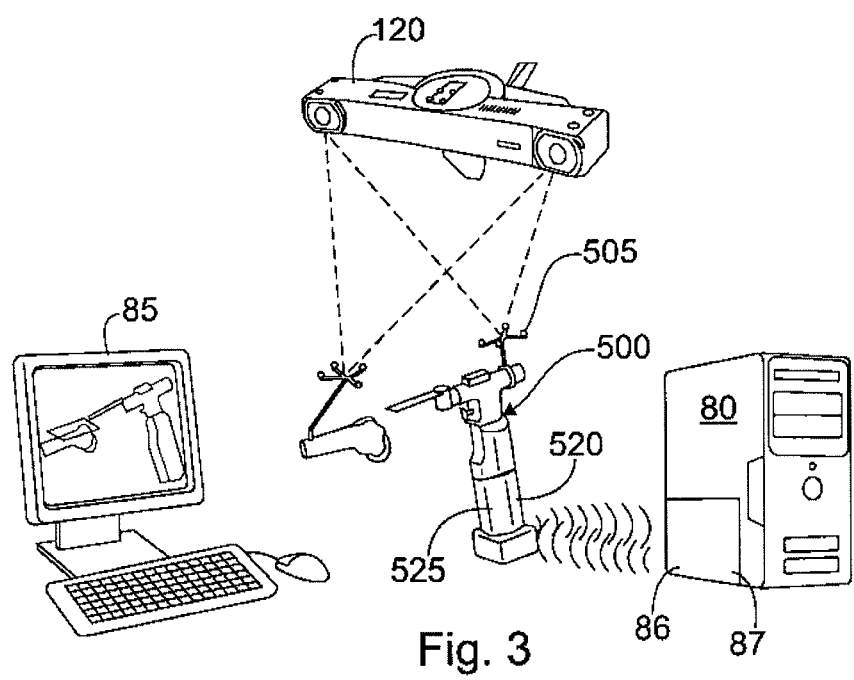
FIG. 3 is an alternative diagrammatic view of a computer assisted surgical suite.

Referring now to the figures, wherein like elements are numbered alike throughout, a surgical suite for computer assisted surgery is designated generally 50. The suite 50 includes a first computer 70 for pre-operative use. For example, pre-operative analysis of the patient and selection of various elements may be performed on the first computer. The suite may also include a second computer 80, referred to as the OR computer, which is used during a procedure to assist the surgeon and/or control one or more surgical instruments. In addition the suite may include a computer (standalone or collaborating with 80) mounted on the surgical instrument. First computer 70 is provided in the present instance, but may be omitted in some configurations because the functions of computer 70 are also implemented on OR computer 80, which can be a standalone. Moreover the whole 'pre-surgical planning' may happen instantaneously inside the OR. Nevertheless, if desired for particular applications, first computer 70 may be used. Furthermore, the micro-processing system of the system 50 can reside in the cutting instrument. In such a configuration, the computations and user interface can be performed within a computer on the surgical tool. Such system performs error analysis of location of the cutting instrument relative to the ideal cut to be performed, and displays corrective actions and other information on a screen mounted to the instrument.

The suite 50 may include a tracking/navigation system that allows tracking in real time of the position in space of several elements, including: (a) the patient's structures, such as the bone or other tissue; (b) the navigable surgical tools, such as the bone saw 100, which is controlled by the surgeon based on information from the OR computer 80 or (c) surgeon/assistants system specific tools, such as a pointer, registration tools, or other objects. The OR computer 80 may also perform some control on the cutting instrument trough the implemented of the present configuration of the system. Based on the location of the tool, the system 80 is able to vary the speed of the surgical tool 100 as well as turn the tool off to prevent potential damage. Additionally, the suite 50 may also include a surgical robot 200 that is controlled by the OR computer 80. The features of the navigable tool 100 and the surgical robot 200 may vary. The details of several desirable features are described in greater detail below. The various features can be selected as desired for a particular practice or situation. In the following description, the only surgical instrument shown in figures is the navigated saw 100. Nonetheless, many others instruments can be controlled and/or navigated as explained above, such as a drill, burr, scalpel, stylus, or other instrument. Therefore in the following discussion, the system is not limited to the particular tool described, but has application to a wide variety of instruments.

As discussed further below, one exemplary use of the surgical suite incorporates the use of a virtual model of the portion of the patient upon which a procedure is to be performed. Specifically, prior to a procedure, a three dimensional model of the relevant portion of the patient is produced using CT scans, MRI scans or other techniques. Prior to surgery, the surgeon may view and manipulate the patient model to evaluate the strategy for proceeding with the actual procedure.

One potential methodology uses the patient model as a navigation device during a procedure. For instance, prior to a procedure, the surgeon may analyze the virtual model of a portion of the patient and map out the tissue to be resected during a procedure. The model is then used to guide the surgeon during the actual procedure. Specifically, during the procedure a tracking mechanism monitors the progress of the procedure and the results are displayed in real time on the OR computer 80 so that the surgeon can see the progress relative to the patient model.

Referring to FIGS. 1-2, to provide navigation assistance during a procedure, the system 50 includes a position detection device 120 that monitors the position of the surgical tool 100. The surgical tool 100 includes one or more position markers 105 that identify pre-defined points of reference on the tool. In the present instance the surgical tool includes several markers 105 which, together with some pre-defined points of reference on the tool, identify the tool and its location.

Although a variety of position tracking systems can be used, one exemplary system is the NDI Polaris optical measurement system produced by Northern Digital Inc. The system uses a position sensor and both active and passive markers. The active markers may be wired sensors that are electrically connected to the system. The active markers emit infrared light that is received by the position sensor. The passive markers are wireless markers that need not be electrically connected to the system. The passive markers reflect infrared light back to the position sensor. Typically, when using passive markers, the position sensor floods the field of view with infrared light that is then reflected back to the position sensor from the passive markers. The position sensor includes an infrared receiver and it receives light emitted light from the active markers and reflected light from the passive markers. The position system triangulates the three dimensional position of the tool based on the position of the markers. In the present instance, the position detection device 120 is also operable to detect the orientation of the tool relative three orthogonal axes. In this way, the position detection device 120 determines the location and orientation of the tool 100.

The position detection device 120 is linked with the OR computer 80 so that the data regarding the position of the surgical tool 100, the patient's anatomy, and other system specific tools, is communicated to the OR computer. The computer uses this information to track the progress of a procedure.

Figure 4:
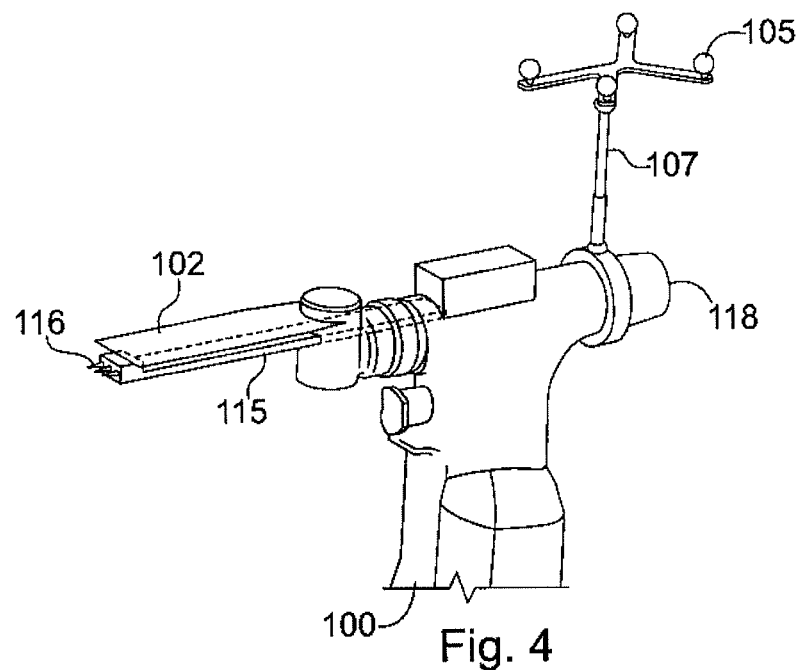
FIG. 4 is a fragmentary view of a surgical tool of the surgical suite of FIG. 1.

To track the position of the surgical tool 100 relative to the patient, a position marker is attached to the portion of the patient on which the procedure is to be performed. The position marker attached to the patient may be similar to the position marker 105 attached to the surgical tool 100, as shown in FIG. 4. The position marker on the patient is correlated to a corresponding point on the virtual model of the patient. In this way, the registration point positions the tool relative to the patient and the patient relative to the virtual model.

A series of points are used to register or correlate the position of the patient's anatomy with the virtual model of the patient. To gather this information, a navigated pointer is used to acquire points at an anatomical landmark or a set of points on a surface within the patient's anatomy. A process referred to morphing may be used to register the patient to the virtual model of the patient. During such a process, the surgeon digitizes parts of the patient and some strategic anatomical landmarks. The computer 80 analyzes the data and identifies common anatomical features to thereby identify the location of points on the patient that correspond to particular points on the virtual model.

Accordingly, as set forth above, the position detector monitors the position of several items in real time, including: the position of the surgical tool 100, the position of the patient and the position of items used during a procedure, such as a pen or marker as described further below. Accordingly, the computer combines the data regarding the position of the surgical tool 100, the data regarding the position of the patient, and the data regarding the model of the patient. This combination is used to provide a real time model of the position of the tool relative to the patient, which can be viewed by the surgeon on the monitor. Further still, as previously described, prior to a procedure, the surgeon may analyze the patient model and identify the tissue that is to be resected. This information can then be used during the procedure to guide the surgeon.

During the procedure, the monitor displays a model of the surgical tool relative to the patient model, which reflects the real time position of the tools, such as the surgical tool 100, relative to the patient. The surgeon can align the position of the tool 100 by viewing the position of the image of the tool relative to the patient model on screen. Once the monitor shows the virtual tool to be aligned with the portion of the patient model identified for resection, the surgical tool is properly aligned on the patient. In this way, the doctor can align the tool without the need for complex jigs or fixtures. Further, as the tool 100 intersects the patient, the data regarding the position of the tool and the patient model is correlated to show the result of the tool intersecting the patient. In this way, the computer can analyze and display the progress of a procedure in real time. As the tool 100 cuts patient tissue, the monitor displays the tissue being removed from the patient model. Therefore, in addition to guiding the position of the tool, the OR computer can be used to guide the surgeon as to what tissue should be resected during a procedure.

In addition to including a surgical tool controlled by the surgeon, the suite 50 may include a surgical robot 200. The surgical robot can be programmed to perform one or more operations during a medical procedure. The surgical robot 200 is controlled by the OR computer, which is programmed with the instruction set for the procedure. As with the navigation system described above, when using the robot, the position detection device 120 monitors the position of the surgical robot, and prior to the procedure the location of the patient is identified so that the computer has data regarding the position of the surgical robot relative to the position of the patient.

Controlling the Selection of View

As previously discussed, information regarding the position of the surgical instrument can be combined with a model of the patient to guide the surgeon during a procedure. During a particular step in a procedure, the surgeon may desire to see a particular view or perspective with a certain combination of orientations of the patient model and the instrument, as well as two dimensional projections. For example when making planar bone cuts using an oscillating bone saw, the system may show simplified two dimensional views along with a three dimensional view. The simplified two-dimensional diagrams may be similar to those displayed on aircraft cockpits or flight simulators, which help align the cut and correct roll and pitch of the saw relative to the plane to be cut. Such diagrams dynamically update in real time and can be shown on the main display of the system and/or a secondary screen, including one mounted on the cutting instrument itself. Although a surgeon may desire to have control over the view, the surgeon normally does not want to be encumbered by manipulating system controls during a procedure. Accordingly, the system is configured to quickly and efficiently automatically change the relevant views and perspectives of the surgical scene. Additionally, the system allows the surgeon to manually select any view/perspective the surgeon may desire.

In the present instance, the system is operable in three modes:
a) manual view selection;
b) pre-set view selection; and
c) automatic view selection.

Each of these is described further below.

Manual View Selection

In the manual view selection mode, the surgeon selects from among numerous parameters to define the exact view that the surgeon desires. The parameters include: the orientation (therefore perspective) of the 3D surgical scene as rendered on the computer screen in the form of an "image", the orientation of the patient model, the surgical instrument to be illustrated, the zoom ratio of the image, the panning position of the image, the transparency of the patient anatomy models, the transparency of the surgical instrument, and the coloring of various items on the screen. These parameters are only examples of the types of parameters that that the surgeon can control to define a view. The system may include many other parameters that the surgeon can control.

In the manual view selection, the surgeon selects and adjusts one or more of the parameters to define the view. For example, the system may include controls to rotate the image about one or more axes. The surgeon may rotate the image through varying degrees about one or more axes to display a particular orientation to see a particular feature of the patient. In this way, the surgeon can precisely define the orientation of the image. In addition to controlling the image orientation, the surgeon can control any other parameter to define a view.

The system may include a variety of input devices in addition to or instead of a typical computer mouse and/or keyboard to allow the surgeon to enter the information to define the parameters for a particular view. For instance, the view screen may be a touch screen and the surgeon may enter the information through one or more menus. Alternatively, the system may include a voice recognition element so that the surgeon may enter the parameters by voice. Further still, the surgical instrument itself may be configured with controls that can be used to enter information regarding one or more of the parameters. In short, the system may include one or more of a variety of interfaces to allow the surgeon to input information to control the parameters that define a view.

Pre-Set View Selection

Although the manual view selection mode provides precise control of the various parameters that define the view for an image, the manual mode can be cumbersome if the surgeon must manually define the parameters for each view during a procedure. To make the view selection easier for the surgeon, the system may also include a pre-set view selection mode.

In the pre-set view selection, the surgeon selects a view from a list of pre-set views. A pre-set view is one in which the parameters that define a view have been previously selected. The pre-set views are either programmed as defaults for the system, or are added as custom views by the user. For instance, a pre-set view may show the patient model in a particular orientation or perspective at a particular zoom and pan, with a particular bone transparency and coloring. Since the parameters are pre-set, the surgeon can simply select a pre-set view to see the image model. In this way, the surgeon can easily select from a number of views to quickly and easily view the patient model under a variety of conditions.

By way of a simple example, in the case of a procedure to implant a knee prosthetic, the pre-set views may include a set of views of the femur, such as an anterior view, a posterior view, a medial view, a lateral view, and a distal view. The surgeon can quickly select from among these orientations simply by selecting one of the pre-set views. In this example the views are defined by the orientation of the patient model, however, each pre-set view includes a number of pre-set parameters (such as a suitable pan, zoom, relative transparency of the different objects, etc), the combination of which is designed to provide an optimized graphical environment for a particular bone preparation/cutting part with the surgical instrument, bone cut assessments, measurements, etc.

As described above, the system may include a variety of different elements to allow the surgeon to select those parameters for the view. For instance, the system can use computer voice recognition or a touch screen or controls mounted directly on the surgical instrument to input data regarding the view. Any of these or other input mechanisms can be used to allow the surgeon to select a pre-set view.

After the surgeon has selected a pre-set view, the surgeon may then manipulate one or more parameters to alter the view. Referring again to the list of pre-set views for a knee procedure, the surgeon may select an anterior view that illustrates, for example, the front of the femur. The pre-set view may be defined such that the patient model is illustrated at 100% magnification. After selecting the pre-set view the surgeon may alter the view to increase the zoom to 200% magnification. The surgeon can make this change using any of a variety of controls that the system may include, as discussed above.

In the present instance, the system also includes the ability to add a view to the list of pre-set views. For example, as described above, the surgeon can use the manual view selection mode to define a view and then save the view as a pre-defined view. Similarly, the surgeon may select a pre-set view and alter one or more parameters to create a new view. The surgeon may then save the new view as an additional view.

For instance, as described above, the surgeon may select a pre-set view entitled anterior view to show the front of the femur. After increasing the magnification of the pre-set view to 200%, the surgeon may choose to save the new view as "enlarged anterior view". Therefore, the surgeon can readily bring up the anterior view with the magnification at 200% simply by selecting the view entitled "enlarged anterior view". Although this example demonstrates how a pre-defined view can be created to provide a view with a different magnification, it should be appreciated that a new view may be defined having whatever combination of parameters the surgeon desires.

Automatic View Selection

Although the pre-set view mode makes it easier for a surgeon to select a desired view during a procedure, the surgeon must still take the step of selecting the view that the surgeon wants displayed. Since a surgeon normally will frequently switch among various views during different steps of a procedure, it may be desirable to provide an easier way of switching the view during a procedure. Therefore, the system may also include a mode in which the view is automatically selected by the computer depending on what part of the bone preparation process the surgeon intends to perform.

In the automatic view selection mode the system automatically selects which view to show based on the current location of the surgical (or measuring) instrument relative to the bone. Specifically, as discussed previously, the system includes a mechanism for tracking the location of the surgical instrument relative to the patient. In response to the data regarding the position of the surgical instrument relative to the patient, its previous location, its approach to a new location and its motion, the system determines what the surgeon is attempting to do. The system then determines the appropriate/optimal view, and shows the view on the display.

Referring again to the example of the knee procedure discussed above, if the surgeon positions the surgical instrument so that the cutting blade is close to the anterior portion of the femur and the plane of the blade of a cutting saw is approaching parallel to one of the desired planar cuts (such as the anterior cut), the system will detect the proximity of the instrument relative to the patient, and the orientation of the blade relative to the patient. Based on the proximity, orientation, and approach of the instrument to the anterior portion of the femur, the system will select the optimum view for this cutting process and show that view on the view screen. In this case that optimum could be (but not limited to) a sagittal view (lateral or medial) of the femur with pan, zoom and other transparency settings of bone and blade to focus on the anterior cut being performed. If the surgeon moves the surgical instrument so that the cutting blade is approaching closely and in the right orientation to perform the posterior cut of the femur, the system will sense the change in position and change the view to show the view appropriate for that specific cut.

Although the system has been described as automatically selecting a view in response to the position of the surgical instrument, other data can be incorporated into the determination of the view that is automatically selected. The additional data may be information input into the system by the surgeon or otherwise. For example, referring again to the knee example, the surgeon may prefer to see the "enlarged anterior view" when the surgical instrument is adjacent the anterior portion of the femur rather than the default "anterior view". Therefore, the surgeon may input information directing the system to use the "enlarged anterior view" instead of the default "anterior view".

Accordingly, during the procedure, when the surgical instrument is adjacent the anterior portion of the end of the femur, the system determines that the "enlarged anterior view" should be shown. This determination is made based on the combination of the data regarding the position of the surgical instrument and the data regarding the preferences of the surgeon.

Since the system can account for the preferences of a surgeon, it is desirable to store the preferences for each surgeon in a user profile. As a surgeon saves pre-set views, the data regarding those pre-set views are added to a user profile for the surgeon and attributed or mapped to the exact types/steps of the procedure. Therefore, prior to performing a procedure, the surgeon selects the appropriate user profile and the data regarding the surgeon's preferences is loaded into the system.

In the foregoing discussion, the surgeon took the effort to input the data regarding the preferences. Alternatively, the system may track a surgeon's usage to learn the preferences of a surgeon. This data is then used to control the image viewed during the automatic view selection mode.

Specifically, the system can track data that is generated during a procedure and identify data that affects the view desired by a surgeon. One way that the system can track usage data is to identify correlations between the position of the surgical instrument and input received from the surgeon regarding the desired view.

For example, as discussed above, a surgeon may routinely switch to an enlarged view when the surgical instrument is adjacent the anterior portion of the femur. By tracking the data regarding the relative position of the surgical instrument and the input from the surgeon regarding the desired view, the system can learn that the surgeon desires to see an enlarged view when the surgical instrument is adjacent the anterior portion of the femur. Therefore, during a procedure, when the user profile for the surgeon is loaded into the system, the system automatically displays an enlarged anterior view rather than the default anterior view when the surgical instrument is adjacent the anterior portion of the femur.

The above example illustrates how the system can track data regarding a surgeon's use to automatically change the perspective/orientation of the scene, its pan, and zoom ratio of an image during automatic view selection mode. It should be understood however, that this is just a simplified example to illustrate a few parameters that the system can track to learn a surgeon's preferences. In actual practice, the system may track data regarding any number of the various parameters that the surgeon may control during a procedure. By tracking and processing the data, the system can learn various data about a surgeon usage. This data is indicative of a surgeon's preferences. By storing and using this data, the system can learn a surgeon's preferences and use the data regarding the preferences to control the image displayed during the Automatic View Selection mode. The data-set representing a given surgeon's user profile for a certain procedure can be transformed/loaded to be used for another surgeon should they desire this, and if they have permission. This is useful in training; to provide the know-how from expert surgeons to novice surgeons. The preferences of which exact views (and all detailed parameter combinations) to use during a given step of a surgical procedure can help novice surgeons start from an optimized set of views and improve upon them to suit their individual preferences.

In case of a newer user of the system who has not defined preferences, the system will provide a default standard set, which is based on experiments and the experience of other surgeons collected by the developers of the system. As explained above, this default set can be modified/customized/enhanced afterwards by the new user.

Bone Removal Simulation and Graphical Identification of Regions

As described previously, the present system 50 can be utilized to perform guided freehand surgery. Specifically, a virtual representation or model of a portion of a patient is provided, along with a model of the surgical tool to guide the surgeon during a procedure. The patient model may include a portion identified as tissue to be resected or otherwise operated on during a procedure. The system tracks the movement of the surgical tool 100, so that when the surgeon moves the tool, the system displays the movement of the tool in real time on a monitor, along with showing the removal of tissue that is resected in response to the movement of the tool. Accordingly, the surgeon can align the tool with the patient by aligning the model of the tool with the portion of the patient model identified for resection. Therefore, the surgeon can follow the onscreen guidance to resect a portion of tissue.

The system may be configured to include various improvements to the processing and graphical representation of the patient model to improve the guidance and/or assistance that the system provides to the surgeon. For instance, various regions of the patient model may be graphically represented in different ways to aide the surgeon in viewing the patient model. One way the system can do this is to display different portions of the patient model in different colors. The different portions of the model are selected and assigned the various colors based on the procedure to be performed, as well as variables that are controllable by the surgeon.

In one example, the system identifies various regions of a patient model based on a prosthetic to be implanted into a patient. The region to be resected will be determined based on the configuration of the prosthetic, variables specific to the procedure (e.g. whether the implant is to be cemented or not), and preferences of the surgeon that may be input into the system or stored in a user profile. Based on these and/or other variables, certain regions of the patient model may be identified as tissue to be resected. Certain other regions may be identified as tissue that may be resected; and certain other regions may be identified as tissue that should not be resected.

By identifying the various regions of the patient model, the system can use this information to display the patient model in a manner that improves the surgeon's ability to process the graphical data. For instance, the regions of the virtual model representing tissue that should be resected can be illustrated in a first color, such as green, The regions of the virtual model representing tissue that may be resected, but do not need to be resected, can be illustrated in a second color, such as yellow. The regions of the patient model representing tissue that should not be resected can be illustrated in a third color, such as red. There could also be a gradient applied to the transitions from the boundary of one region to the boundary of the adjacent region. The color gradient would create a gradual change in color from one region to the next. For instance, the boundary area between the green region and the yellow region may be colored to follow a color gradient from green to yellow. The color gradients aide the surgeon in identifying transitions from one region to another.

Alternatively, the different regions may be represented by uniform colors without color gradients between regions. In some instances, the use of uniform colors rather than color gradients can create a contrast that provides an alignment aide for the surgeon to use. The surgeon may align the surgical tool with a plane represented by the intersection of two regions. The color contrast of the different regions may create an easy to read graphical representation that the surgeon can use for alignment.

In addition to providing alignment, the difference in color between the regions serves as an indication to the surgeon to proceed more slowly as the tool approaches the resection boundary. When resecting a portion of a bone a surgeon may cut more rapidly and aggressively when the cutting tool is relatively far from the boundary of the area to be resected. As the surgeon approaches the boundary of the resection area, the surgeon may slow the pace of cutting to ensure that the resection remains within the desired boundaries. By illustrating the different regions in different colors (or otherwise), the system provides a readily identifiable graphical display that informs the surgeon of the proximity of the surgical tool to a resection boundary.

Similarly, the system can be used to identify the proximity of the surgical tool to sensitive anatomical structures, such as nerves, vessels, ligaments etc. The anatomical structures can be illustrated in red and the tissue proximate the structures can be identified in yellow as an indicator to the surgeon that the cutting tool is getting close to the sensitive structure.

As discussed above, the contrasts between different representations of different regions of a patient model can be helpful to guide the surgeon in aligning the surgical instrument during a procedure. To further improve the alignment of the surgical instrument with a particular plane, the graphical representation of the surgical instrument may be altered. More specifically, the boundaries of the surgical instrument may be elongated along a line or along an entire plane.

For instance, in the case of a bone cutting saw, the blade is a generally rectangular thin flat blade having a height, length and thickness or gauge. The thickness is normally the smallest of the three dimensions. When viewing the model of the blade on edge, the edge of the blade will generally look like a thick line. To improve the guidance provided to the surgeon, the height and length of the blade may be elongated. By elongating or enlarging the representation of the blade, the surgeon can more easily identify the plane of the blade to ensure that the plane of the blade is aligned with the proper plane for a cut. The extensions are particularly helpful in illustrating whether the cutting blade is rotated relative to a desired plane.

The graphical extensions for the blade may be illustrated in the same color and style as the blade. In the present instance, the graphical extensions have some characteristics that are similar to the surgical instrument, but there are one or more characteristics that differ. For example, in the present instance, the cutting tool may be displayed on the screen as an opaque yellow item. The extensions may be a similar color but they may be semi-transparent, so that the surgeon can easily recognize that the extensions are related to the blade, while also easily distinguishing which part represents the cutting tool and which part represents the extensions.

The system may provide controls to allow the surgeon to control characteristics of the extensions, such as the extent of the extensions (i.e. how much elongation along the height, how much elongation along the length), the color of the extensions and the opacity of the extensions, as well as other characteristics. The controls also allow the surgeon to manually turn the extensions on and off.

In addition to manually controlling the characteristics of the extensions, the characteristics of the extensions may be defined by pre-set views. The operation of pre-set views are described in detail above. As an example of controlling the extensions using pre-set views, in a first pre-set view, the extensions may be illustrated in a certain manner with a certain color and opacity. In a second pre-set view, the extensions may not be displayed at all. By switching between the first and second pre-set views, the surgeon can control the display of the extensions. Further, as discussed above, the system may be configured to automatically change between pre-set views based on the location and/or orientation of the surgical instrument. Therefore, the pre-set views can be defined so that the extensions are automatically turned on or off depending on the location and/or orientation of the surgical instrument.

As an alternative to illustrating the extensions as simply planar extensions, the cutting tool and/or extensions cutting blade may be illustrated as an oval on the display. The shape of the cutting blade then depends on the angle of the cutting blade relative to the proper plane. If the cutting blade is aligned properly, the cutting blade will look similar to a line. As the cutting blade is twisted relative to the proper cutting plane, the cutting blade appears more rounded and oval. In this way, the variation between the angle of the cutting blade and the angle of the proper cutting plane is readily apparent based on the ovality of the cutting tool on the display.

The option of displaying the blade as an oval is another choice that can be selected for a particular view. Therefore, in one view, the blade may be illustrated without any extension. In another view, the blade may be illustrated with planar elongations. In yet a third view, the blade may be represented as an oval. The surgeon may switch between these representations within a view, or the representations may be defined in one or more pre-set views.

In the description above, different regions of the patient model are identified and are illustrated differently to aide the surgeon during a procedure. In addition to providing a graphical representation of the different regions, the system may use the data regarding the different regions to provide a graphical and/or audible warning to the surgeon. For instance, as the system detects the surgical tool approaching the area proximate the resection boundary (e.g. the yellow zone), the system may display a graphical warning on the monitor 85 in addition to illustrating the surgical tool in the yellow zone of tissue on the model. Alternatively, or in addition to the graphical warning, the system may provide an audible warning indicating that the cutting tool is approaching the desired boundary. The system may provide yet another warning in the event the cutting tool is detected at or beyond the desired boundary. In other words, if the surgical tool enters the red zone the system may provide a further warning.

In addition to providing warnings, the system may be configured to control the operation of the surgical tool in response to the position of the surgical tool relative to the desired boundary. Specifically, if the system determines that the tool is positioned within the tissue to be resected (e.g. in the green zone), the system may allow the surgical tool to be controlled as desired by the surgeon. If the system determines that the tool is positioned within the tissue that may be resected but is near the tissue that is identified as tissue that should not be resected (e.g. the yellow zone), the system may reduce or attenuate the operation of the surgical tool. For instance, if the tool is a saw, and it enters the yellow zone, the system may slow down the reciprocation of the saw as it moves close to the resection boundary. Further still, if the system detects that the tool is positioned at the boundary or in tissue that is not to be resected, the system may completely stop the tool. Although the system may automatically control the operation of the surgical tool, the system includes an override function that allows the surgeon to override the control of the tool. In this way, if the surgeon determines that a portion of tissue should be resected that was not previously identified for resection, the surgeon can override the system and resect the tissue during the procedure.

In the discussion above, the system controls the display of various regions based on an identification of the regions prior to a procedure. The system may also allow regions to be identified and/or re-assessed during a procedure. For instance, as described in the section regarding assessment of bone preparation, the system may include features relating to assessing the cuts made during a procedure to determine whether further cuts need to be made. In response to the assessment, the system may determine which portions of the bone need to be cut to correct an inaccuracy in a resection procedure. This correction assessment may cause a change in the regions of the patient to be resected, which will cause a change in the identification of various portions of the patient model. For example, a region that was initially identified as a yellow region may be changed to a green region after the correction assessment. In this way, the identification of regions of a patient model may change during the course of a procedure.

In the foregoing description the operation of the surgical instrument is controlled based on the region in which the instrument is operating. Additionally, the operation of the surgical instrument may be controlled based on how far into a region the instrument has traveled. For instance, the surgical instrument may not need to be significantly attenuated when it just enters the yellow region. However, the instrument may need to be significantly attenuated if it advances significantly through the yellow region toward the red region. Accordingly, the magnitude of control may relate to both the region that the instrument is positioned within and the degree to which the instrument extends into the region.

Navigated Marking Pen

As described previously, the OR computer 80 may display a virtual model of the portion of the patient on which the procedure is to be performed. In the discussions above, the patient model was utilized to guide the surgeon in manipulating surgical tool to perform a procedure. The following discussion describes how the patient model can be used to guide the surgeon in preparing the site for a procedure. Specifically, the system may guide the surgeon in marking lines on the patient to identify cut lines etc. for a procedure. The markings on the patient can then be used alone or in combination with the guided freehand procedure described above.

Figure 13:
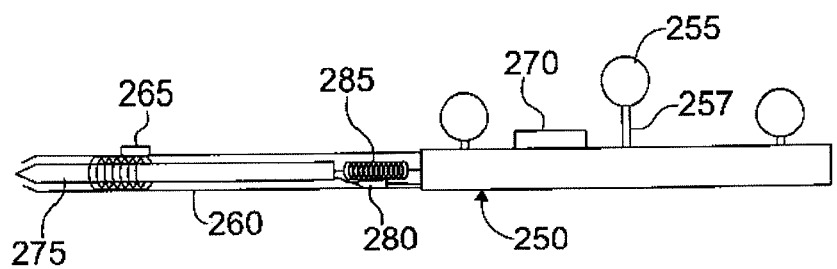
FIG. 13 is a diagrammatic illustration of a navigable marking pen.

Referring to FIG. 13, a navigated marking pen 250 is illustrated. The marking pen 250 includes one or more elements for detecting the position and orientation of the marker. For instance, the marking pen may include a reference frame 257 and a plurality of position markers 255 similar to the frame 107 and position markers 105 described above in connection with the surgical tool. The marking pen 250 can be guided by viewing the display of the OR computer 80 as described above in connection with operation of the surgical tool 100. The marking pen 250 is guided to draw lines on the bone at the appropriate locations as identified on the virtual model.

The method for using the navigable marking pen 250 operates as follows. Prior to the procedure, a virtual model of the relevant portion of the patient is created as discussed above. The surgeon analyzes the patient model to determine the procedure to be performed and identifies the portion of the patient to be resected or otherwise operated upon during the procedure. For instance, in the instance of implanting a prosthetic device, a femoral prosthetic may be implanted. The surgeon selects the appropriate prosthetic and aligns a model of the prosthetic over the operation site. Based on the model of the prosthetic and the alignment, the Pre-op computer 70 may identify the tissue to be resected during the procedure. Prior to the procedure, the patient is registered as described previously, so that the patient position corresponds to the patient model.

The OR computer 80 displays the patient model, identifying the tissue to be resected, and the position of the marking pen is also illustrated on the display. As the surgeon manipulates the marking pen 250, the position detection device 120 detects the movement of the marking pen and provides data to the OR computer so that the model of the marking pen moves on the screen relative to the patient model in real time. Accordingly, the surgeon manipulates the marking pen so that the model of the marking pen aligns with the portion of the virtual model indicated for resection.

The surgeon manipulates the marking pen 250 so that the model of the marking pen traces the area of the virtual model identified for resection or other procedure (such as drilling). In this way, the virtual model provides a guide for guiding the surgeon to mark the appropriate areas on the patient on which the procedure is to be performed. The surgeon may then simply perform the procedure freehand using the markings on the patient as a guide or the surgeon may perform the procedure using the markings and also using freehand navigation assistance as described above.

FIG. 13 also illustrates another potential improvement, in that the marking pen 250 may include a retractable pen that retracts when the marking pen is not aligned with the proper area on the patient. By retracting, it is much less likely that the surgeon may mark an incorrect area.

As shown in FIG. 13, the marking pen 250 includes a hollow housing 260 having a generally open forward end. A displaceable pen 275 is disposed within the hollow housing 260. The pen is displaceable between an extended position and a retracted position. In the extended position the tip of the pen extends from the housing so that the tip of the pen can be used to mark a surface. In the retracted position the pen is retracted into the housing so that the forward tip of the pen is within the housing so that the pen cannot mark a surface.

A spring 285 connected to the pen 275 biases the pen toward the retracted position. An actuator 280, such as a solenoid is operable to extend the pen forwardly against the bias of the spring. Specifically, when the solenoid is energized, the solenoid drives the pen to the extended position. When the solenoid is de-energized, the spring 285 retracts the pen into the housing. Alternatively, the solenoid can be configured to drive the pen in both directions, i.e. the solenoid can drive the pen forwardly and rearwardly as desired.

The marking pen 250 is in communication with the OR computer 80 to receive signals indicating whether the pen 275 should be extended or retracted. The marking pen may include a wired connection to the OR computer, however, in the present instance, the OR computer 80 includes a transmitter, and the marking pen includes a wireless receiver for receiving signals from the computer. The marking pen 250 includes a processor 270 for receiving the signals from the computer and controlling the extension and retraction of the pen 275 in response to the signals. Specifically, the processor 270 controls the operation of the solenoid to selectively energize and de-energize the solenoid in response to signals received from the OR computer.

The operation of the retractable marking pen 250 is similar to the operation described above. However, the OR computer correlates the data from the virtual model with the data regarding the position of the marking pen. If the OR computer determines that the marking pen is positioned over a portion of the patient that should be marked, the computer transmits a signal to the marking pen 250 indicating that the pen should be extended. The marking pen receives the signal and the processor 270 controls the solenoid, thereby energizing the solenoid to extend the pen tip 275. If the OR computer determines that the marking pen is positioned over a portion of the patient that is not to be marked, the computer transmits a signal to the marking pen indicating that the pen should be retracted and the processor controls the solenoid to retract the pen. Alternatively, the processor may be configured so that the solenoid is energized only as long as the controller receives a signal indicating that the pen should be extended. In this way, the OR computer sends a signal to the marking pen as long as the computer determines that the marking pen is over a portion to be marked. As soon as the computer determines that the marker is over an area that is not to be marked, the computer ceases sending a signal to the marking pen. The processor then de-energizes the solenoid to retract the pen in response to the lack of signal.

As an alternative to a retractable tip, the marker may use an inkjet, rather than a regular marker tip. Rather than controlling the extension or retraction of the marker tip, the ejection of the ink through the inkjet is controlled. Specifically, when the marker is over a portion of the portion of the patient to be marked, the marker may be enable so that ink may flow through the inkjet. However, when the marker is over a portion of the patient that is not to be marked, the marker is disabled, so that the flow of ink to the inkjet is shut off.

As can be seen from the foregoing, the marking pen 250 can provide an accurate and efficient method for marking cut lines and other marking lines for performing a procedure. Prior to the procedure, the surgeon may utilize the guidance system to manipulate the marking pen by aligning the model of the pen with the area of the virtual model to be operated on. While the surgeon maintains alignment of the virtual pen with the portions of the model indicated as proper marking lines (such as the outline of a prosthetic), the OR computer sends a signal to the marking pen indicating that the pen element 275 should be extended. As the surgeon maintains the virtual pen aligned on proper parts of the virtual model, the marking pen 250 marks the patient. If the surgeon manipulates the pen so that the virtual pen moves out of alignment with the proper parts of the virtual model, the OR computer sends a signal to the marking pen (or ceases sending a signal to the pen as described above), and the pen tip 275 retracts into the housing so that the pen stops marking the patient. In this way, the surgeon controls the retraction of the pen by maintaining alignment of the virtual pen with the portion or portions of the model that were identified as portions to be marked.

Registration Pointer with Surface Contact Detection

Prior to or during a procedure, a digitizing pen or pointer may be used to identify the location of points of reference on a patient. Similarly, the pointer may be used to mark areas to identify a surface. The marked points identify the location of discrete points or areas on a patient to correlate or register the patient model with the actual position of the patient.

Although a pointer can be helpful in registering the location of a patient, human error can lead to errors in properly registering the patient location. For instance, when the surgeon is tracing the surface of the patient tissue, the tip of the pointer may come out of contact with the surface of the tissue. This is particularly true when tracing over soft tissue or when tracing along curved surfaces. If the pointer is not in contact with the surface of the tissue, the resulting data points will be erroneous.

To improve the accuracy of the data collected during registration, the system may include a pointer that incorporates a sensor that detects whether the pointer is in contact with the patient tissue. If the pointer is out of contact with the surface of the relevant portion of the patient, the points are ignored during the registration analysis. Additionally, the system may provide feedback to the surgeon to warn the surgeon that the point is out of contact with the patient tissue.

Figure 15:
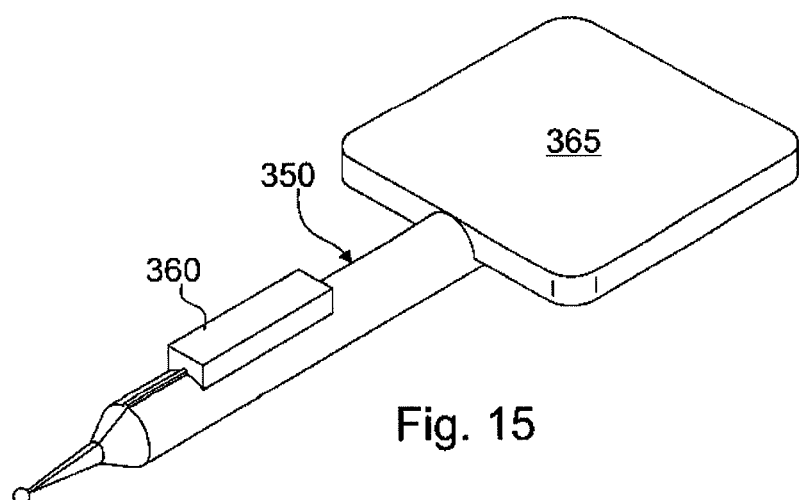
FIG. 15 is a registration pointer operable in connection with the surgical suite illustrated in FIG. 1 or FIG. 3.

Referring to FIG. 15, an improved registration pointer is designated 350. The pointer is an elongated element having a tip configured to contact the relevant portion of a patient. The pointer 350 is operatively linked with the position detection device 120. The operative link may be a wireless connection in which the pointer includes a wireless transmitter. Alternatively, the pointer may be connected directly to the detection device via a cable.

The pointer includes a sensor 360 for detecting whether the tip of the pointer is in engagement with the patient or whether the tip of the pointer is spaced apart from the patient. One possible sensor 360 is an impedance sensor. Alternatively, the sensor may be a simple force transducer. The pointer 350 includes a circuit 365 for analyzing the signal from the sensor and determining whether the pointer is in contact with the patient surface based on the signal from the sensor.

The data for the point or points in which the pointer was out of contact with the patient surface are not utilized during the registration process. Specifically, the pointer circuit may identify valid and invalid data by various means. According to a first method, the pointer communicates the relevant data to the OR computer 80 via a wired or wireless connection. Alternatively, the pointer circuit may control the position tracking elements so that the pointer is out of view of the position detection device 120 when the pointer 350 is out of contact with the patient surface.

According to the first method, the OR computer receives signals from both the pointer 350 and the position detection device 120 and processes the data. The pointer circuit provides a signal to the OR computer indicating whether the pointer is in contact with the patient tissue. The OR computer 80 receives the signals from the pointer circuit 365 along with signals from the position detection device 120 that indicate the position of the pointer. Based on the signal received from the pointer 350, the OR computer 80 either accepts or rejects the position data received from the position detection device 120. For instance, if the surgeon is tracing the pointer over an area of tissue, the OR computer will accept the position data regarding the area traced by the pointer as long as the sensor 360 detects that the pointer tip is in contact with the patient. If the sensor 360 detects that the pointer is out of contact, the OR computer discards or rejects the data from the position detection device 120 corresponding to the positions that the sensor detected the pointer is out of contact. In this way, as long as the pointer remains out of contact with the patient surface, the OR computer discards the corresponding position data from the position detection device.

The system may be configured to process the signals from the pointer 350 and the position detection device 120 in a variety of ways. For instance, the OR computer may reject data from the position detection device unless the pointer sensor 360 provides a signal indicating that the pointer is in contact with the patient tissue. Alternatively, the OR computer may accept data from the position detection device unless the pointer sensor 360 provides a signal indicating that the pointer is out of contact with the patient tissue. In either alternative, the OR computer only records data for points in which the pointer is in contact with the patient tissue.

In an alternative embodiment, the OR computer does not reject the data to eliminate erroneous data. Instead, the system alters the position detection device 120 to prevent the erroneous points from being detecting.

Specifically, the system controls features of the position detection device 120 to essentially make the pointer disappear from view of the position detection device when the pointer is out of contact. Since the pointer is out of view when it is out of contact with the patient, no data is collected while the pointer is out of contact.

The steps for rendering the position detection elements out of view of the detector varies depend on the type of detection element. For instance, as described previously, the position detection device may operate in conjunction with passive and active markers. An active marker is a marker that transmits an infrared signal to the detection device and the position of the marker is identified by triangulating the received signal. Accordingly, to control the active marker(s), the pointer circuit 365 controls the active markers by turning off the active markers so that they no longer emit an infrared signal when the pointer is out of contact with the relevant portion of the patient. When the emitter ceases emitting infrared light, the marker is hidden from the position detection device 120 so that the registration points are not detected.

If the markers on the pointer are passive elements, the markers are detected by detecting the infrared light reflected back to the position detection device 120. In order to hide such passive markers the pointer circuit may be used to control one or more elements including a displaceable opaque surface and an electronically/chromatically actuated effect to disable the infra-red reflectivity of the ball. Accordingly, for both passive marker systems and active marker systems, the system may control the position detection device 120 in response to signals from the pointer 350 indicating that the pointer is out of contact with the patient tissue.

In addition to controlling whether or not data points are accepted or rejected, the system may provide feedback to the surgeon warning that the pointer is out of contact with the patient tissue. For instance, if the sensor 360 on the pointer 350 indicates that the pointer is out of contact with the patient tissue, the pointer circuit 365 may provide a signal to an indicator light, such as an LED on the pointer. Therefore, if the surgeon sees the LED illuminated, the surgeon will recognize that the pointer needs to be pressed against the patient. Alternatively, the signal from the sensor circuit can be communicated with the OR computer, so that a warning is displayed on the display screen. In addition to providing a visual warning, the system may provide an audible warning. Specifically, the pointer circuit 365 may provide a signal to an audio element to provide a warning signal, such as a beep when the pointer is out of contact with the patient.

There may be instances in which the pointer is out of contact with the patient so often that it may be desirable to re-start the registration process. Accordingly, the system may track the number of times that the sensor 360 detects that the pointer is out of contact with the patient. If the number of times exceeds a pre-set threshold, the system may send a warning to the surgeon indicating that the registration process should be re-started.

Combination Cutting and Filing Blade

Figure 18:
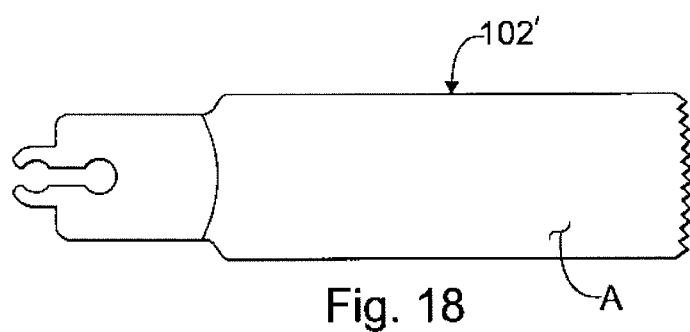
FIG. 18 is a top view of an alternative cutting blade operable in connection with a surgical saw.
Figure 19:
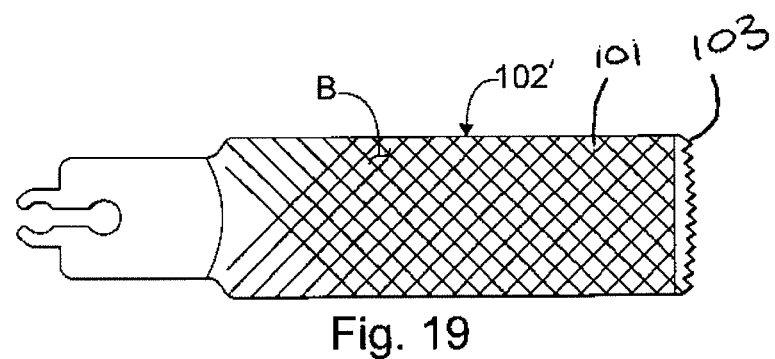
FIG. 19 is a bottom view of the cutting blade illustrated in FIG. 18.

Referring to FIGS. 18-19 an alternate cutting blade 102' is illustrated. The cutting blade 102' includes both an edge that can be used for cutting, as well as a surface that can be used for filing. Specifically, the cutting blade 102' has a cutting edge with a plurality of cutting teeth 103. The teeth are formed in a row and may have a set. The row of teeth are operable to cut when the blade is reciprocated. The blade also includes a surface that can be used for filing, such as filing a bone surface during a procedure.

As shown in FIGS. 18-19, the blade has two sides, A and B. Side A is a generally smooth surface. Side B is on the side opposite from side A, and is formed with a plurality of cutting surfaces that form a filing surface. Specifically, side B is a generally elongated planar surface having a length and a width. A plurality of spaced apart ridges or teeth 101 protrude upwardly from the surface of the blade. Each ridge extends across the width of the blade so that the ends of each ridge terminate at the edges of the blade. However, the ridges 101 need not extend across the entire width of the blade.

The ridges 101 on side B of the blade 102' form a secondary cutting surface that can be used for different procedures than the row of cutting teeth 103. Specifically, the row of teeth 103 can be used to make a cut in a bone. In contrast, the ridges 101 form a filing surface that can be used to file a bone surface.

Further, the cutting blade 102' can be used in a computer assisted technique, similar to those described above. The row of teeth can be used in a computer guided procedure in which the computer aligns the cutting blade to cut a portion of bone. Similarly, the filing teeth can be guided using a computer guided procedure in which the computer guides the filing teeth to remove a portion of bone that is identified for removal.

Tool Registration Head

One step during navigated surgery is the registration of the surgical tools. Registration is the process of identifying the specific location and orientation of a surgical tool. If a tool is not properly registered the navigation of the tool will be flawed leading to errors during the procedure.

As discussed previously, the system may provide guidance by displaying a graphical illustration of the position of the surgical instrument relative to the patient. The system provides this guidance by tracking the location and orientation of the surgical instrument. For example, in the present instance, the surgical instrument 100 includes a frame having a plurality of markers 105 that are used to track the position and orientation of the surgical instrument. By tracking the location and orientation of the reference frame, the system can track the location and orientation of the surgical instrument. Since the structure of the surgical instrument is generally fixed relative to the reference frame, identifying the location and orientation of the reference frame can be used to identify the location and orientation of the surgical instrument.

Although the configuration and dimensions of the surgical instrument are generally fixed, the surgical instrument may be used with one or more of a variety of different cutting tools or accessories during a procedure. For instance, the surgical instrument may use any of a number of different sized saw blades or drill bits. Since the tool is typically the part of the surgical instrument that actually operates on the patient tissue, it is important to accurately identify the configuration of the tool, as well as the location and orientation of the tool.

To properly track the position of the tool during a procedure, the registration process identifies the configuration of the tool, as well as the location and orientation of the tool relative to the position detection element(s) on the surgical instrument. Specifically, the registration process identifies the position and orientation of the tool relative to the frame and markers 105 on the surgical instrument 100.

Figure 14:
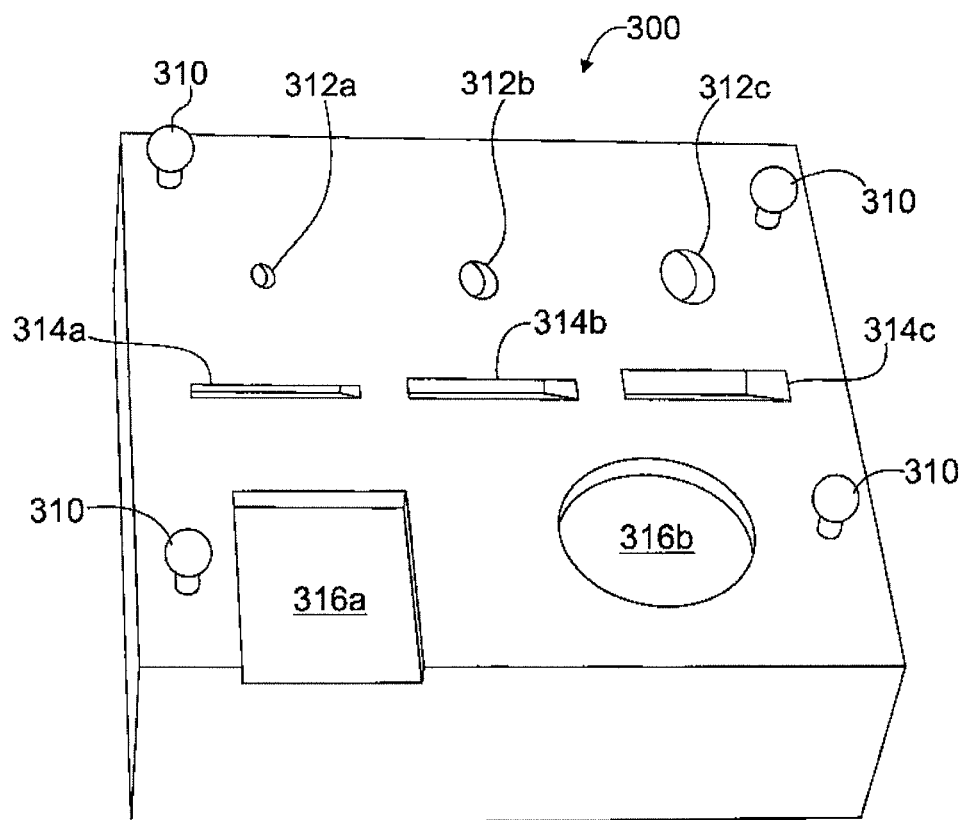
FIG. 14 is a registration block for registering tools of a surgical instrument.

Referring to FIG. 14, a tool registration head 300 is illustrated. The registration head 300 is designed to quickly and easily register a tool so that the system can accurately track the position and orientation of the tool. In this way, the registration head allows a surgeon to change tools during a procedure without the undue delay involved in known processes for registering a tool.

In the following discussion, the registration head 300 is described in connection with registering a variety of cutting tools. However, it should be understood that this is an example of one type of tools that the registration head may be configured to register. The registration head can be configured to register any of a variety of cutting tools and/or accessories that can be used in the surgical instrument.

The registration head 300 includes a plurality of sockets that are configured to mate with a plurality of cutting tools that can be used in the surgical instrument. The sockets are configured so that each socket cooperates with a particular tool. In this way, the system identifies the tool type in response to a determination of the socket into which the tool is mounted. In the present instance, the registration head 300 includes three rows of sockets. The first row 312a,b,c is configured to register drill bits. The second row 314a,b,c is configured to register saw blades; and the third row 316a,b is configured to register other tools.

The first row includes three sockets, 312a, 312b and 312c. Each socket is cylindrical having a different diameter. In this way, inserting a tool in the first socket 312a registers the tool as a drill bit having a particular diameter, inserting the tool in the second socket 312b registers the tool as a drill bit having a particular diameter, which in the present instance is larger than the diameter of the first socket. As can be seen, the registration block may have a series of numerous cylindrical sockets for registering numerous different drill bits. Each socket would have a different diameter for registering a particular diameter drill bit.

The second row of sockets in the registration head 300 is configured to register saw blades, such as sagittal blades. Such blades are generally thin flat blades having a row of teeth on one end. The second row of sockets includes a first socket 314a in the form of a rectangular slot having a height and width. The height corresponds to the thickness of a particular saw blade and the width corresponds to the width of the saw blade. Therefore, inserting a tool into the first saw blade socket 314a registers the tool as a sagittal blade having a predetermined width and thickness. Similarly, inserting a tool into the second saw blade socket 314b registers the tool as a sagittal blade having a predetermined width and thickness that is larger than the blade corresponding to the first saw blade socket 314a. As with the sockets for the drill bits, it should be appreciated that the registration block can include a number of different sized slots configured to mate with numerous different saw blades. Each slot would be configured to mate with a specific saw blade so that the blade can be uniquely identified and registered by simply inserting the blade into the appropriate slot.

In addition to the sockets, the registration head 300 also includes a plurality of position detection elements 310. The position detection elements may be either passive marker elements or active marker elements, as discussed previously. The type of position detection elements is selected to cooperate with the tracking system 120 that is used. For instance, in the present instance, the registration head 300 includes a plurality of spaced apart spherical reflective markers 310.

The spacing and the orientation of the position detection elements 310 are known. Therefore, the tracking system 120 can determine the position and orientation of the registration head 300 by detecting the location of each position detection element 310. Additionally, the position and/or configuration of the registration sockets in the head 300 is known.

Accordingly, as described above, the tracking system 120 can track the position detection elements 310 on the registration head 300 to determine the position and orientation of the registration block. Similarly, the tracking system 120 can track the position detection elements 105 on the surgical instrument 100 to determine the position and orientation of the surgical instrument. Since each socket in the registration head defines a unique location for a particular tool, the position of the surgical instrument relative to the registration block is unique for each particular tool. The unique spacial relationships between the registration block and the surgical instrument is predetermined for each tool that the registration block is configured to register.

Part of the information that is determined during the registration process is the position of the tip of the tool relative to the position detection elements 105 on the surgical instrument. As discussed above, the configuration and orientation of each tool relative to the surgical instrument can be determined depending upon the socket into which the tool is inserted. However, this process does not necessarily identify the position of the tip of the tool. For instance, if a tool is registered when the tool is inserted only halfway into a socket, the system will incorrectly assume that the tip of the tool is at a position corresponding to where the tip would be if the tool was fully inserted into the socket.

To properly identify the location of the tip of a tool, each socket has a bottom wall that acts as a stop. The location of each bottom wall is a fixed location relative to the position detection elements 310, which is pre-determined for the registration head. Since it is a fixed and known location, the bottom wall operates as the assumed location of the tip of the tool when a tool is inserted into a socket. Therefore, to properly register a tool, the tool is inserted into a socket until the tip of the tool engages the bottom wall of the socket.

Based on the foregoing, a tool, such as a saw blade can be easily registered by simply attaching the tool to the surgical instrument 100 and then inserting the tool into the proper socket in the registration head 310. The tool is fully inserted into the socket until the tip of the tool engages the bottom of the socket. During the registration process, the tracking system 120 tracks the position and orientation of the registration block relative to the surgical instrument, which identifies the configuration and orientation of the tool relative to the position tracking elements 105 on the surgical instrument. For instance, in the case of a saw blade, if the blade is inserted into slot 314a, the relative position between the registration block and the surgical instrument identifies the tool as a saw blade having a particular height and width. Furthermore, the saw blade fits into the slot in a particular orientation, so the orientation of the blade is also know.

In other words, the tracking system 120 tracks the position detection elements 310 to track the position and orientation of the registration head. The tracking system also tracks the position detection elements 105 on the surgical instrument to determine the position and orientation of the surgical instrument. As discussed previously, the spacial orientation between the surgical instrument and the registration block is pre-determined and unique for each socket. Therefore, when a tool is inserted into a socket in the registration head, the spacial orientation between the surgical instrument and the registration head 300 defines the boundaries of the tool relative to the tracking elements 105 on the surgical tool. Accordingly, after the tool is registered, the system can accurately track the boundaries of the tool mounted in the surgical instrument by tracking the position of the tracking elements 105 on the surgical instrument.

The process for registering a tool may be either manual or automatic. In a manual mode, the tool is inserted into the proper socket until the tip of the tool contacts the bottom wall of the socket. While the tip is in contact with the bottom wall of the socket, the surgeon presses a button to indicate that the tool is properly registered in a socket. The system uses the positional data from the tracking system 120 at the time when the button was pressed to determine the position of the tracking elements 310 on the registration head 300 and the position of the tracking elements 105 on the surgical instrument 100. Based on the position data, the system calculates the location of the boundaries of the tool relative to the tracking elements 105 on the surgical instrument.

In addition to pressing the button, the indicator signal for registering a tool can be other various forms of inputs. For instance, the input signal could be a voice signal that is recognized be voice recognition software. Alternatively, the input signal could be an area on a touch screen, a click of a mouse, an input mechanism on the surgical instrument itself, a keyboard stroke or otherwise.

In an automatic mode the surgeon need not press a button to indicate that the tool is inserted into the registration head 300. Instead, the system automatically determines that the tool is inserted into a socket and makes the registration calculations.

One automatic mode relies upon sensors in the registration head 300. Specifically, a sensor is located in each socket of the registration head. The sensors may be any of a variety of types of sensors, such as an impedance sensor or a load transducer. The sensor detects whether a tool is in contact with the bottom wall of the socket. When the sensor detects that the tool is in contact with the bottom wall, the sensor sends a signal to the OR computer or the tracking system 120. The signal from the sensor operates similar to the surgeon pressing the button in the manual mode described above.

A second automatic mode may be used instead of the first automatic mode described above. The second automatic mode automatically registers the tool without using sensors in the registration head. In the second mode, the tool is inserted into the registration head 300 and is held in the appropriate socket for a pre-determined time period, such as 1 or 2 seconds. The system tracks the location of the surgical instrument relative to the registration block and registers the position of the tool when the surgical instrument is at a fixed position for the pre-determined time period. In this way, the period of time that the surgical instrument is stationary relative to the registration block operates as the trigger for registering the tool.

Although the second automatic mode may use a hold time as the trigger, the system may need to ignore positions that do not correspond to valid registration positions. For instance, if the surgical instrument is stationary on a surface sitting next to the registration head, the tool will be stationary for a sufficient period to trigger registration. However, when the surgical instrument is sitting next to the registration head, the position of the surgical instrument relative to the registration block does not correspond to a valid registration position. Therefore, in the second automatic mode, the system may reject registration data corresponding to positions that are invalid registration positions.

In another alternative mode, rather than rely on a hold time as the trigger, the system may simply evaluate the positional data to register a tool. Specifically, the system may monitor the position of the surgical instrument relative to the registration head to determine which of the sockets the tool is inserted into, as described above. As the tool is inserted into the socket, the surgical instrument will move in a particular direction. For instance, in the example of registering a drill bit, the surgical instrument will move towards the registration block along an axis as the drill bit is inserted into the corresponding socket. Assuming that the surgeon inserts the tool until it touches the bottom wall of the socket, the registration position will relate to the maximum point of travel along the axis. As with the second mode above, the system will ignore data that does not correspond to a valid orientation of having a tool inserted into one of the sockets.

Once the tool is registered, the system tracks the boundaries of the tool by tracking the location of the tracking elements 105 on the surgical instrument. If the surgeon desires to use a different tool during a procedure, the surgeon simply needs to replace the tool with the new tool, indicate to the system that a new tool is to be registered, such as by pressing a button or otherwise, and then inserting the new tool into the appropriate socket in the registration block as described above. Since the registration process is quick and easy, the overall procedure is not significantly delayed when a new tool is needed.

As discussed above, the positional data regarding the dimensional configuration of the registration block is predetermined, as is data regarding the positional relationship between the surgical instrument and the registration block for each socket. This data is stored in either a file on the OR computer or the position detection system 120. Similarly, data regarding each type of tool that correlates to each socket may be stored in a data file on the OR computer.

Assessing and Correcting Bone Cuts

When implanting a prosthetic onto a bone, the surgeon must resect portions of the bone to prepare the bone to receive the prosthetic. Regardless of how the resection is performed, it is helpful to assess the quality of the cuts performed during a procedure prior implanting the prosthetic. Bad fit between the bone and the prosthetic causes a significant number of implant failures. Therefore, a close match between the shape and dimensions of the prepared bone and the prosthetic is important to the proper affixation and durability of the implant. The surgeon may rely upon experience and trial and error during a procedure, however, doing so does not provide a quantifiable method for ensuring that a resection is proper.

Accordingly, it may be desirable to incorporate a method and apparatus for assessing the quality of bone cuts before a prosthetic is implanted. Additionally, after assessing the bone cuts, it may be desirable to provide feedback regarding any additional shaping that should be made to improve the bone cuts to prepare the bone to receive the implant.

The assessment of bone cuts evaluates four aspects: surface finish, fit, alignment and accuracy. The surface finish relates to the smoothness of the cut surfaces. The fit relates to how closely the bone shape matches the shape of the implant. The alignment relates to whether or not the cuts are made so that the implant is positioned in the proper three rotations of alignment, including the flexion/extension axis, the anterior/posterior axis, and the proximal/distal axis. The accuracy relates to the angle and orientation of each cut relative to the plane of the ideal cut.

During a procedure, bone is resected according to the geometry of the prosthetic to be implanted. After the resection, the cut bone is analyzed to evaluate the four aspects mentioned above: surface finish, fit, alignment, and accuracy.

Referring to FIG. 1, the system for assessing the bone cut comprises a scanning device 320 that communicates with a processor, such as a personal computer, which may be the OR computer 80. The processor communicates with an output device, such as a monitor 85 to illustrate information about the assessment of the bone cuts.

The scanning device 320 may be one of a number of various devices for acquiring information. For instance, the scanning device 320 may be a probe such as the smart probe discussed above. The probe is traced over the cut surfaces to obtain data regarding each surface.

Analysis of Surface Finish

Figure 10:
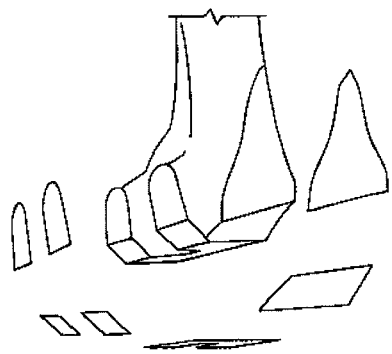
FIG. 10 illustrates the femur cuts for a total knee replacement procedure.
Figure 11:
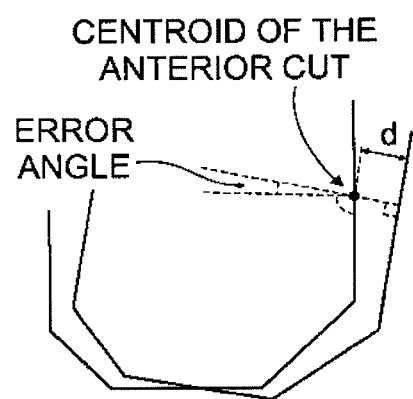
FIG. 11 is a diagram illustrating the error angle for bone cuts in a total knee replacement procedure.
Figure 12:
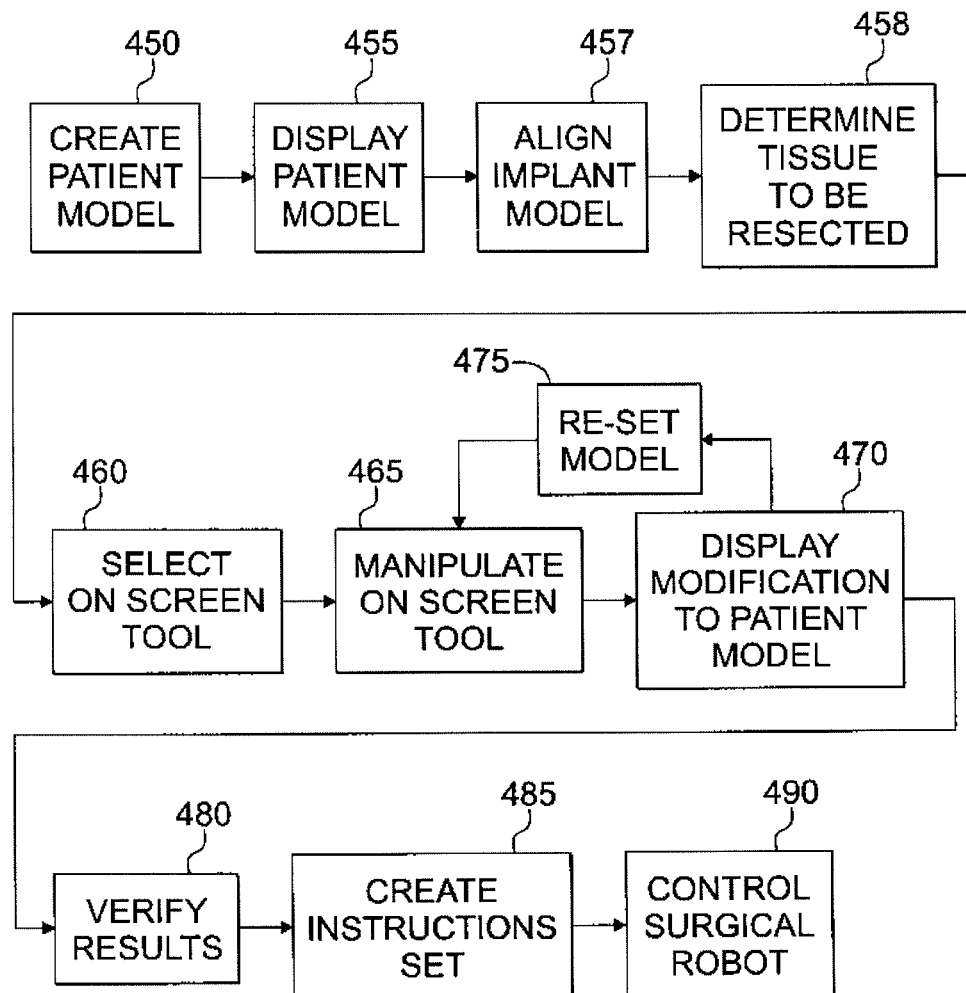
FIG. 12 is a diagram illustrating the steps of a method for programming a surgical robot.

The processor analyzes the scanned data to evaluate each cut of the resected bone. For instance, as shown in FIG. 10, in the case of a TKR procedure, there are typically five separate cuts made to the femur when the bone is resected to accommodate the prosthetic (it may be considered seven cuts rather than five when considering the posterior condyle resection as two cuts, as well as the posterior chamfer). The image data for the resected bone is analyzed to assess the surface finish for each of the five cuts.

Figure 7:
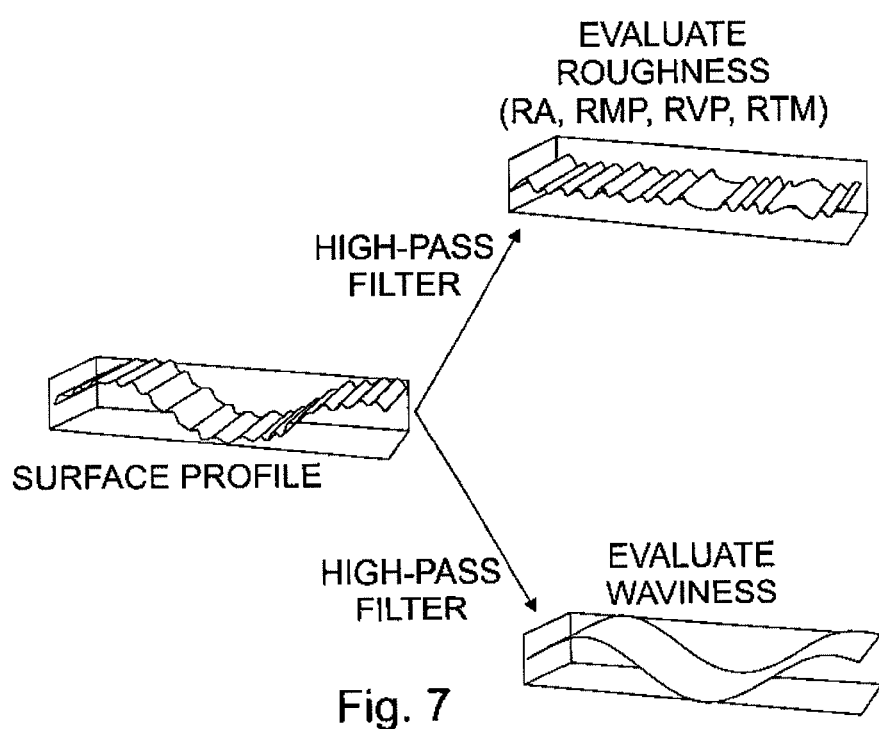
FIG. 7 illustrates a separation of the surface waviness and surface roughness of a surface profile.

The analysis of surface finish may include an analysis of one or more characteristics to evaluate whether the surface is of sufficient quality to bond well with the prosthetic. In the present instance, the system analyzes the roughness and/or the waviness of the resected surface to assess the surface finish. Roughness includes the finer irregularities of a surface that generally result from a particular cutting tool and material conditions. Waviness includes the more widely spaced deviation of a surface from the nominal or ideal shape of the surface. Waviness is usually produced by instabilities, such as blade bending, or by deliberate actions during the cutting process. As illustrated in FIG. 7, waviness has a longer wavelength than roughness, which is superimposed on the waviness.

Figure 8:
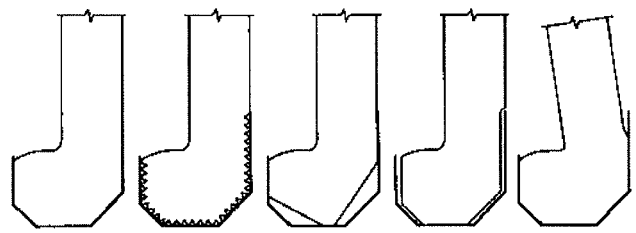
FIG. 8 is a table illustrating the various potential error in fitting an implant.
Figure 9:
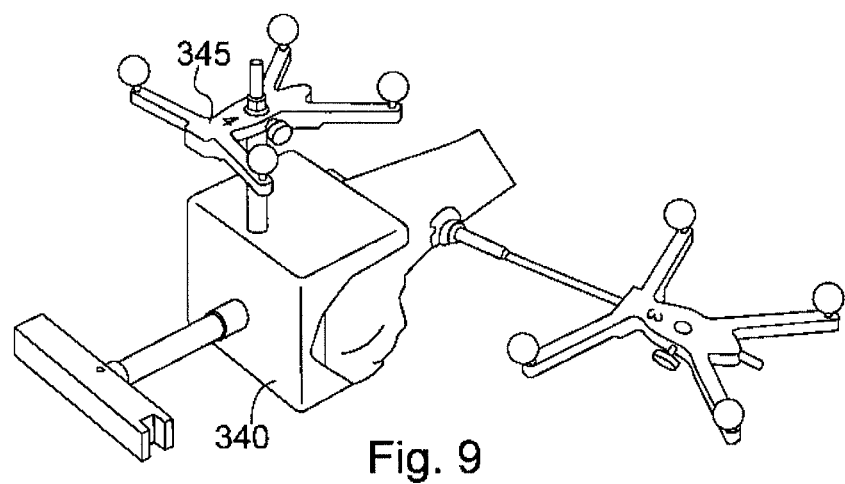
FIG. 9 is a measuring block for assessing the fit of an implant.

Based on analysis of the 3D geometrical image data, the surface finish for each cut is analyzed and quantified. In the present instance, the surface finish may be quantified based on: (1) the roughness average, (2) an average of the heights of a select number of the worst peaks (i.e. highest surface peak relative to ideal surface); (3) an average of the heights of a select number of the worst valleys (i.e. deepest valley relative to ideal surface); and (4) a measure of the deviation from the average height of the worst peaks and the average depth of the worst valley (i.e. (2)-(3)). In some instances, it may be desirable to separate the quantification of the measure of waviness from the measure of roughness. However, in the present instance, roughness and waviness are evaluated together. An example of a resected femur having unacceptable surface finish is illustrated in FIG. 8. As can be seen, the geometry of the resection is proper, so that the prosthetic would fit properly onto the resected bone and be properly aligned. However, due to the poor surface finish it is likely that the bond between the bone and the prosthetic will fail prematurely. Based on the surface finish analysis, the surgeon may decide that one or more of the cuts may need to be smoothed, such as by filing.

Analysis of Fit

The second characteristic evaluated for the bone cuts is fit. Fit represents the looseness or play between the implant and the resected bone shape prior to affixing the prosthetic to the bone. An example of a resected femur having an unacceptable fit error is illustrated in FIG. 8. As can be seen, the surface of each cut is acceptable and the orientation of each cut is acceptable, however, the resultant shape leaves unacceptable gaps between the prosthetic and the resected bone.

The gaps create play or looseness that will lead to misalignment and/or premature failure of the bond between the bone and the prosthetic.

To measure the fit error, a fitness measuring block 340 may be utilized. The fitness measuring block 340 is a block having an internal shape corresponding to the internal shape of the prosthetic (i.e. the surface that will bond with the bone). A tracking element 345 for detecting displacement is attached to the fitness measuring block. In the present instance, the tracking element is an infrared tracking device similar to the frame and markers 105 that are used to track the surgical instrument, as described above. Alternatively, a navigated implant trial that is specific to each prosthetic implant may be used rather than a measuring block. The navigated implant trial is an implant similar to the prosthetic that is to be implanted into the patient. The navigated implant would also include an element for detecting the position of the implant trial, such as the tracking element 345 described above. The tracking system 20 (see FIG. 1) tracks the position of the tracking element 345 and communicates data to the processor that is indicative of displacement of the measuring block 340 relative to the resected bone.

To use the measuring block 340, the block is placed over the resected bone. The surgeon then attempts to move the measuring block in all directions relative to the bone to evaluate translational error based on the amount of translation possible between the measuring block and the resected bone. Specifically, the surgeon rotates the block in flexion and extension, as well as internally and externally. In other words, the surgeon rotates the blocks about several axis relative to the bone, such as an axis running generally parallel to the axis of the bone (i.e. rotation internally and externally) as well as an axis running generally transverse the axis of the bone (i.e. rotation in flexion and extension).

As the surgeon moves the measuring block, the tracking system 120 tracks the translational and rotational movement of the measuring block relative to the bone. The tracking system communicates the data regarding the movement of the measuring block with the OR computer 80. Based on the data from the tracking system 120, the OR computer analyzes and quantifies the fit based on the measured translational error and the measured rotational error. Specifically, the OR computer 80 analyzes the data regarding movement of the measuring block to measure extremes of movement of the measuring block relative to the bone. The extremes of movement are measured in each of six direction of movement/rotation. The extremes of motion indicate the looseness of the fit. If the measuring block can move significantly relative to the bone, then the extremes of movement will be significant. This will reflect a loose fit. Conversely, if the measuring block cannot move significantly relative to the bone, then the extremes will be relatively small. This will reflect a tight fit.

Analysis of Alignment

A third characteristic for assessing the cuts is the alignment of the cuts. The alignment assessment can be performed using the same data set that was collected while analyzing the implant fit as described above.

The alignment error is a quantification of the deviation of the location of the measuring block from the ideal location at which the implants are to be positioned for proper alignment. Specifically, in the present instance, the alignment error is based on three rotational deviations and three translational deviations from the ideal locations.

The deviations of the measuring block from the ideal position(s) are based upon the data obtained by the tracking system 120 during tracking of the measuring block to evaluate the fit, described above. The OR computer 80 analyzes the data regarding the movement of the measuring block relative to the resected bone. The OR computer 80 analyzes the data to evaluate whether the measuring block passed through the ideal alignment position as the block was moved between the extremes of movement.

If the measuring block passes through the ideal alignment during the test manipulation, the alignment is correct; if not, the alignment is off. To evaluate the alignment error, the computer analyzes the data from the tracking system to determine how close the measuring block came to the proper alignment position. This deviation is analyzed for the six parameters about the three rotational axes mentioned above.

In other words, for each axis of rotation, the system determines the position that the measuring block should pass through to be ideally aligned in the axis of rotation. The system determines how close the measuring block came to the ideal position when the block was rotated along the same axis of rotation. The deviation is analyzed for each axis to obtain an overall error measurement.

Analysis of Accuracy

A fourth characteristic used in the present instance to evaluate the bone cuts is the accuracy of each cut. For example, in the instance of a TKR procedure, the accuracy of each cut is evaluated. The importance of the accuracy of the cuts is exemplified by the third sample illustrated in FIG. 8. As can be seen, the sample has acceptable surface finish, fit and location. In other words, the prosthetic will fit well on the bone (i.e. it won't wiggle excessively), the surface finish is not too rough or wavy and the prosthetic will be properly aligned with the bone. However, due to the inaccuracy in one or more of the cuts, there will be gaps between the prosthetic and the bone that will increase the likelihood of premature failure.

To evaluate the accuracy of the cuts, the deviation between the actual cuts and the ideal cuts for the particular prosthetic is measured. The ideal cuts are determined based on the geometry of the prosthetic to be implanted on the resected bone. For instance, in the example of a TKR, the ideal cuts for the femur are based on the internal configuration of the femoral prosthetic. One way of determining the ideal cuts is to create a model of the configuration of the ideal cuts for the patient.

In the present instance, a scanner can be used to create a three dimensional model of the resected bone, as discussed further below. The data obtained from the scanner for each planar resected surface is compared with the data for the corresponding surface of the ideal resected model to evaluate the accuracy of the cuts. The quantification of the accuracy can be based on a variety of measurements regarding the deviation of each resected surface from the ideal surface.

To assess accuracy, the plane of each cut is calculated using a best fit plane. The deviation of the best fit plane from the ideal plane is analyzed to determine accuracy. Specifically, in the present instance, four characteristics are measured to assess accuracy. The first characteristic is a translational measurement, and it is calculated as the distance between the best fit plane of the resected surface and the centroid of the corresponding ideal cut. The remaining three characteristics are rotational angles. The first rotational characteristic is the orientation of the resected surface relative to the ideal plane with respect to a first axis; the second rotational characteristic is relative to a second axis and the third rotational characteristic is relative to a third rotational axis. These characteristics are measured and correlated to quantify the accuracy of each planar cut of the resected bone.

Each cut is analyzed independently in the accuracy assessment. Therefore, the assessment can be used to detect which adjustments need to be made to a cut if the cut exceeds an error threshold. The system can suggest one or more cuts or modifications to be made based on an analysis of the resected bone and the ideal cuts.

In the foregoing description, the evaluation of the location error and fit error are based on measurements provided by manipulating the fit measurement block 340 relative to the resected bone. Alternatively, the fit and location errors may be evaluated using a virtual comparison of the resected bone and models of ideal location and fit for the bone. For instance, the resected bone may be scanned to create a three dimensional model of the resected bone. The scanner may use electromagnetic, ultrasonic/acoustic, mechanical, infrared line-of site, or other elements. For instance, a three dimensional optical laser scanner, scriber, navigated digitizer, coordinate measuring machine or CT-based digitization can be used to create a digital model of the bone surface.

Prior to the procedure a three dimensional model of the relevant portion of the patient can be created using any of a variety of techniques, including but not limited to CT scans and MRI images. The processor may include a database of models corresponding to various prosthetics. The surgeon selects the appropriate prosthetic model and positions it relative to the model of the relevant portion of the patient. The processor then modifies the patient model to reflect the ideal resected surfaces for the selected prosthetic. Using collision detection algorithms, the scanned data for the resected bone can be compared with the data for the model for the ideal resected bone to calculate the various criteria used to measure fit error, alignment error and/or accuracy error.

Feedback from Assessment

After the processor determines the various criteria to assess the quality of the cuts, the information regarding the criteria may be displayed on the monitor to indicate to the surgeon whether or not the cuts were of sufficient quality to proceed with implanting the prosthetic on the bone. Additionally, if the cuts are not of sufficient quality, the processor may evaluate the cuts to determine a strategy for modifying the resected bone to improve the quality of the cuts. For instance, based on a comparison of the scanned data for a resected bone with the data for the model of an ideal resected bone, the processor may determine the portion(s) of bone that should be re-shaped to improve the correlation between the resected bone and the model for the ideal resected bone. After determining the portions of the bone that should be re-shaped, such changes are displayed on the monitor to show the surgeon which portion(s) of the bone should be removed. For example, using a graphical output, the bone may be illustrated generally in white and the portion(s) of the bone that should be resected to improve the fit with the prosthetic may be shown in red.

Intraoperative Surgical Motion Recording

As discussed previously, during a procedure, the tracking system 120 tracks the position and orientation of the surgical instrument 100. This tracking data is used to provide real-time feedback and/or guidance during the procedure. In addition, the system may store the tracking data for later review and/or analysis. For instance, after a procedure, a surgeon can review the stored data to see each step that was taken during a procedure and the order in which each step was taken. Such analysis can provide valuable insight into advantages and/or disadvantages of particular steps of particular procedures.

The tracking system 120 is designed to track the movement of the tracking elements 105 of the surgical instrument. The tracking system is able to track the tilt, roll, pitch and offset of the surgical instrument as it in manipulated. Further, the tracking system 120 is able to track the position, and orientation of the surgical instrument and the speed of movement. Further still, the system is able to track the position of the surgical instrument relative to the bone.

The tracking data is stored, so that it can be re-called to review a procedure. Specifically, the data can be re-called so that each step of a procedure can be reviewed in the sequence that each step was performed during the procedure.

As discussed previously, the tracking system 120 tracks the position and orientation of the surgical instrument 100 and the system correlates the position of the instrument with the position of the patient. The system then displays an illustration of the position of the surgical instrument relative to the patient. Specifically, the system displays a model of the patient tissue and displays a model of the surgical instrument in a position and orientation relative to the model corresponding to the tracked position and orientation of the instrument relative to the patient.

Since the stored data relates to the three-dimensional position and orientation of the surgical instrument relative to the patient, the data can be used to display a three-dimensional representation of the surgical procedure. For instance, similar to the playback of a movie, the stored data can be used to display an illustration of each step in a procedure in the sequence that each step occurred. Additionally, since the tracking data includes three-dimensional information, the illustration is not limited to the view that was displayed during the procedure, as would be the case if a movie was taken of the procedure and then watched later. In contrast, during the review of the procedure, the tracking data can be used to watch a step of the procedure from any desired perspective or view. For example, during a procedure, a certain cut may be guided by viewing the patient model from an anterior view. When reviewing the data stored for the procedure, the user may view the step from a posterior view, or any other view that the user desires. In this way, the user may evaluate each step from any number of perspectives to identify how a step was accomplished and/or the result of a particular step.

The stored tracking data can be used in a variety of applications. For instance, a surgeon may review the tracking data to assess the efficiency or effectiveness of various procedures. Similarly, the data can be used to teach procedures to other surgeons, such as less experienced surgeons. The less experienced surgeon will be able to see exactly what steps were taken and the result of each step and the result of the overall procedure.

In addition, to allowing the review of data from a procedure, the tracking system can be used to simulate a procedure. Using the patient model, the surgeon may manipulate the surgical instrument to simulate the steps taken during a procedure. The system tracks the manipulation of the surgical instrument and illustrates the effect of each manipulation on the patient model. The surgeon can see the effect of each manipulation on the patient model in real-time. In this way, the simulation allows a surgeon to test or evaluate a procedure on a model of the patient. The data regarding the simulation can be recalled during an actual procedure to guide the surgeon.

In the alternative, the stored data can be used to guide a automated surgical instrument, such as a surgical robot. The surgeon can manipulate a surgical instrument to perform a simulated procedure, as discussed above. Once the surgeon has finalized and validated each step in a procedure, the data regarding the position and orientation of the surgical instrument at each step of a procedure is stored. The stored data is then used to guide an automated surgical instrument, such as a robot, to perform the procedure. The automated instrument will follow the guidance of the stored data, so that the surgical instrument is manipulated to track the actions of the surgical instrument during the simulated procedure.

Anchoring Device for Surgical Tool

When performing a navigated freehand, one of the issues is maintaining the alignment of the surgical instrument, particularly during the start of a cut. For instance, at the beginning of a cut the saw blade may tend to wander from the desired cut line or plane. However, once the cut begins, the blade creates a kerf, which tends to limit the movement of the saw blade. Unfortunately, if the saw moves out of alignment at the beginning of a cut, the saw kerf can constrain the saw blade in a plane that is out of alignment, thereby furthering the problem created when the saw moved at the start of the cut. To limit the misalignment that may occur at the beginning of a cut, the surgical tool may includes an anchoring device mounted on the surgical tool.

Referring to FIG. 4, the anchoring device 115 is an elongated element positioned adjacent the cutting tool 102. The forward end of the anchoring device 115 is positioned so that the tip of the anchoring device protrudes beyond the tip of the cutting tool. In the present instance, the anchoring device 115 includes a plurality of pins or spikes 116 positioned at the end of the anchor. The pins 116 are configured to anchor the anchor 115 into bone, and the pins may retract after a cut begins. The anchoring device 115 may also include a recess for receiving the pins 116 when the pins retract so that the pins do not interfere with the cutting operation of the tool.

Although the anchoring device 115 can be configured in a variety of shapes, in the present instance, the anchoring device is an elongated flat bar positioned parallel to the cutting blade 102 and in close proximity to the cutting blade. The anchor 115 preferably is more rigid than the cutting blade, and preferably is substantially rigid relative to the cutting blade. In this way, the anchoring device supports the cutting tool, limiting the deflection of the cutting blade toward the anchor.

During a procedure, the anchoring device operates as follows. As described above, the surgeon views the monitor to properly align the surgical tool to perform the cut. After the surgical instrument is aligned, the surgical instrument is anchored to the bone by driving the instrument toward the patient bone to anchor the pins 116 in the bone. The surgical instrument may include an internal hammering device to lock the anchoring pins 116 to the bone when the alignment is correct, or the surgical instrument can include a portion, such as an anvil 118, that can be hammered to drive the pins 116 into the bone.

Once the anchoring device 115 is driven onto the bone, the anchoring device constrains the movement of the surgical instrument. Specifically, the anchoring device 115 limits lateral movement of the surgical instrument relative to the bone. However, the anchoring device allows the rotational of the surgical instrument relative to the bone, and preferably, at least some axial displacement of the surgical instrument toward the bone. In this way, the anchoring device allows the cutting blade to be aligned and maintained with the proper location to begin a cut. At the same time, the anchoring device 115 allows the surgical instrument to rotate so that the cutting blade can be aligned with the plane of the proper cut and advanced into the bone.

As described below, during a cut, the anchor 115 may be configured to collapse. Accordingly, to anchor the pins into the bone, the anchor 115 includes a brake or a lock to lock the anchor in an extended position while the pins are anchored into the bone.

Once the anchor 115 is anchored to the bone, the surgeon starts the tool and the cutting blade 102 is driven into the bone. The lock or brake on the anchor is released to allow the anchor to collapse during a cut. Specifically, the anchor 115 is configured so that it can collapse or telescope as the saw is moved forward during the procedure. In other words, the pins 116 remain in engagement with the tissue (e.g. bone) and the anchor 115 collapses as the saw move forward relative to the pins. In this way, the pins 116 anchor the cutting blade 102 as the cutting blade progresses through a cut.

Figure 5:
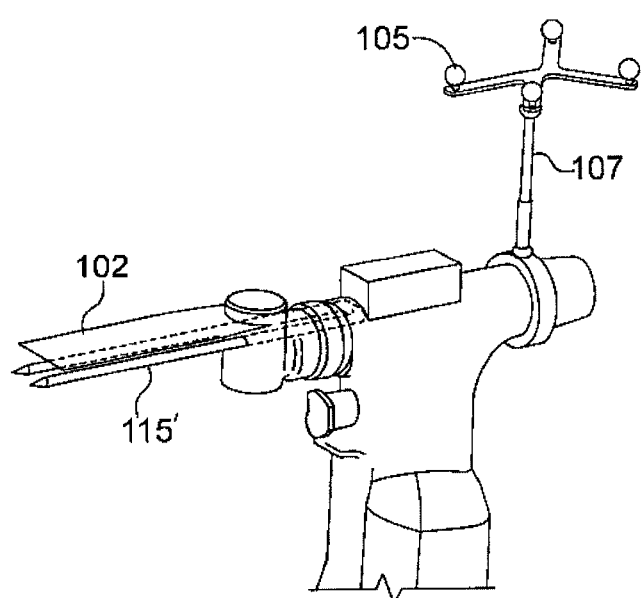
FIG. 5 is an alternative embodiment of the surgical tool illustrated in FIG. 4.
Figure 6:
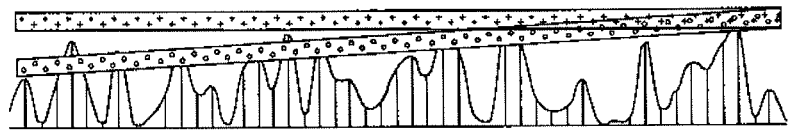
FIG. 6 is plot illustrating data regarding the surface roughness and surface waviness.

As described above, the anchoring device includes a flat bar and retractable pins. However, the configuration of the anchor can vary based on a number of criteria, including, but not limited to design, friction and heat requirements, sterilization needs etc. For instance, rather than being an elongated flat bar, the anchor may comprise a pair of elongated cylindrical rods spaced apart from one another. The ends of the rods may be pointed to facilitate anchoring the anchor into the bone, as shown in FIG. 5.

Additionally, the anchoring device need not include retractable elements. Instead, the anchoring device may be a rigid element that is removable from the surgical instrument. In use, the anchoring device is driven into the bone to anchor the surgical instrument relative to the bone. The surgical instrument is then operated to start a cut. After the cut is started, the surgical tool is withdrawn and the anchoring element is removed from the surgical tool. The saw kerf that was started is then used to guide the rest of the cut.

Tool Bending & Deflection Correction

As described above, the tracking system 120 can be used to detect and monitor the position of either a surgical tool 100 or a surgical robot 200. One issue in correctly navigating the surgical tool or the robot is the need for an accurate assessment of the position and orientation of the surgical tool or robot. Specifically, although a number of markers 105 may be used to identify the position of a tool, markers are typically not applied to the tip of a tool, particularly if the tool is a cutting tool. Instead, the position of the tool is determined and the position of the cutting tip is calculated based on the known geometry of the tool, and the presumption that the tool is a rigid element. However, during use, the tool may deflect or deform so that the actual position of the cutting tip may not correspond to the presumed position of the cutting tip. Therefore, the correlation between the actual tissue being cut and the virtual model do not match. In other words, based on the data received from the position detection device the OR computer 80 may determine that a certain portion of tissue is resected, however, due to tool deflection the actual tissue resected may be different.

The system may compensate for the tool bending or deflection in one of several ways. Using system compensation, the system can monitor and calculate the tool bending, and then manipulate the tracking data to compensate for the calculated bending. Alternatively, using on-board compensation, the compensation calculations are determined and affected on-board the surgical instrument.

Using system compensation, the tool may include a sensor for detecting deflection or deformation of the tool. For instance, referring to FIG. 2, a surgical tool 100 is illustrated, having a cutting blade 102. The surgical tool 100 reciprocates the cutting blade during operation. A sensor in the form of a load-cell 104 included in the saw detects the force and/or torque applied to the blade. Alternatively, a piezoelectric sensor may be connected directly to the blade to detect the force and/or torque applied to the blade. The measured force or torque is used to predict the distance "d" that the blade bends. Specifically, properties of the cutting blade 102 are stored. Based on the predefined cutting tool properties and the measured force or torque, the amount of bending is calculated. The calculated amount of bending approximates the distance "d" and is used as a compensation factor to adjust the position and orientation of the cutting tool detected by the position detection device 120. Specifically, not only will the system process the tracking data to compensate for the position of the cutting tool, the system will also process the tracking data to compensate for the angle of the deflected cutting tool.

The advantage of using system compensation is that the alterations to the surgical instrument are minimized. However, system compensation requires that the system be programmed to alter the processing of the tracking data, as discussed above. While this may not be a barrier for a new system, users that already have a system with a tracking system may be hesitant to adopt a process that requires alteration of the tracking software or the software that processes the tracking data. Accordingly, it may be desirable to make the bending compensation adjustment on board the surgical instrument. The modified surgical instrument can then be used with the user's existing tracking system without any further modifications.

In the on-board approach, the surgical instrument includes an onboard processor that calculates the tool deflection. Based on the calculated deflection, the surgical instrument manipulates the tracking element(s) to compensate for the deflection. In this way, the position detection device 120 will detect the compensated position of the cutting tool, which will reflect the actual position and orientation of the deflected cutting tool.

Referring again to FIG. 2, the surgical tool 100 may include a processor 106 operable to receive signals from the load cell 104 indicative of the force applied to the cutting blade. Based on the data received from the load cell, the processor 106 calculates the deflection "d" of the tip of the cutting tool 102 and the angle at which the blade is deflected. The system, then manipulates the tracking element on the surgical instrument.

In the present instance, the surgical tool includes a reference frame onto which a plurality of markers 105 are mounted. As described previously, the tracking system 120 detects the position of the markers to determine the location and orientation of the surgical tool.

In a system compensation design, the frame is typically rigidly mounted to the surgical tool so that the position of the markers relative to the rest of the tool is fixed. However, as shown in FIG. 2, the frame 107 may be movably connected to the surgical tool 100. Although the freedom of movement of the frame may be limited, preferably the frame is connected to the surgical frame by a connection that provides at least two degrees of freedom, such as a universal joint. Furthermore, in the present instance, the frame is extendable and retractable to alter the length of the frame to properly compensate for the position and orientation of the deflected blade.

Connected to the frame 107 are a plurality of actuators or deflectors 108 that control the position of the frame. The actuators 108 are in electrical communication with the processor 106, and preferably the processor 106 independently controls the operation of each actuator.

The processor 106 controls the operation of the various deflectors 108 based on the signals received from the sensor 104. Specifically, as described above, the processor 106 calculates the deflection "d" of the tip of the cutting tool based on the signal received from the sensor 104. Based on the calculated deflection, the processor determines the appropriate compensation to the position of the frame to compensate for the deflection of the cutting tool 102. The processor then controls the operation of the actuators 108 to re-position the frame. For instance, in the example illustrated in FIG. 2, the cutting tool is deflected an amount "d" in a clockwise direction. Accordingly, the actuators 108 reposition the frame 107 to displace the markers 105 an amount "d" in a clockwise direction. Additionally, the vertical actuator is operated to alter the height of the frame 107 to compensate for the proper plane of the deflected tool. The position detection device 120 then detects the position of the surgical tool at the compensated position so that no further calculations are necessary to monitor the position of the deflected cutting tool.

By utilizing an on board deflection compensation, the system can incorporate deflection compensation, while still allowing the surgical tool to be used with a variety of commercially available position detection devices without the need to modify the software used by such devices.

Although the foregoing example describes the onboard compensation feature as utilizing a plurality of actuators to reposition a reference frame, the configuration of the compensation elements may vary depending on the configuration of the position detection elements used.

For instance, other position detection devices may be used in the system, such as systems that include electromagnetic sensors, ultrasound elements or accelerometers. When such elements are utilized, the compensation features may either vary the position of the element or it may vary the data provided by such elements in response to the data received regarding the load on the cutting tool.

Intelligent Control of Surgical Instrument

As described previously, the present system 50 can be used to perform guided freehand surgery in which a model of the patient is provided, along with a model of the surgical tool and the models can be used to guide the surgeon during the actual procedure. For instance, the patient model may include a portion identified as tissue to be resected. The system tracks the movement of the surgical tool 100, so that when the surgeon moves the tool, the system displays the movement of the tool in real time on the monitor. In this way, the surgeon can align the tool with the patient by aligning the model of the tool with the portion of the patient model identified for resection. In this way, the surgeon can follow the onscreen guidance to resect a portion of tissue.

During the procedure, the system may control or modulate the surgical instrument in response to the position of the surgical instrument. Specifically, as discussed previously, the system may track the position and orientation of the surgical instrument relative to the patient. If the surgical instrument is not in the proper position or orientation relative to the patient, the system may control the surgical instrument, such as by stopping the instrument to ensure that the surgical instrument does not operate on the wrong portion of tissue.

Further still, in an alternate design, the system can intelligently control the operation of the surgical instrument based on additional data, such as the degree of mis-alignment or the location of the incorrectly positioned instrument.

For example, if the surgical instrument is in a position that does not correspond to the desired cut, it may not be a location that warrants automatically shutting off the instrument. For instance, the surgeon may be holding the surgical instrument so that the saw blade is away from the patient and in mid-air. In such a position, the instrument is not in the correct position to make a cut, but the instrument will not to any harm in the air. Therefore, there is no need for the system to control the operation of the instrument. Conversely, if the instrument is positioned adjacent the patient's tissue and it is improperly located and/or oriented. It may be desirable to control the operation of the instrument to prevent the surgeon from cutting tissue erroneously. Accordingly, the system may control the operation of the surgical instrument in response to the location and orientation of the surgical instrument relative to the patient, combined with data about the area around the surgical instrument and whether the area around the surgical instrument can be damaged.

In addition, in some instances, the surgical instrument may not be properly oriented or positioned, however the misalignment/misorienatation may be minor. A minor error may not warrant the degree of automated override that a significant misalignment warrants. Accordingly, the operation of the surgical instrument may be controlled in response to the degree of deviation from the desired position or orientation of the surgical instrument. Specifically, the degree of control may correlate to the degree of error. The greater the error, the greater the control. For example, a minor error in alignment may cause the system to attenuate the rate of the saw by a minor amount, whereas a substantial misalignment of the saw in a critical area of tissue may cause the system to stop the saw.

When controlling the operation of the surgical instrument, the control can either affect the range of modulation or the control can actually modulate the surgical instrument. For example, if the surgical instrument is improperly positioned, the saw may be controlled so that it can only be operated by 0-50% normal speed. In other words, the instrument can be operated in an attenuated range. Alternatively, the instrument could be controlled so that the instrument operates at an attenuated speed, such as 50%.

The control or attenuation of the surgical instrument may be based on control signals received from the OR computer based on pre-defined data for the procedure and data from the tracking system. Alternatively, the surgical instrument may include an onboard processor that determines the proper control based on the tracking data and pre-defined data for the procedure.

Optional Features for the Surgical Instrument

As discussed previously, the surgical instrument 100 includes a cutting tool 102 and a tracking element, such as a frame 107 with passive markers 105, as shown in FIGS. 1 & 2. However, the surgical instrument may include a variety of optional features.

Figure 20:
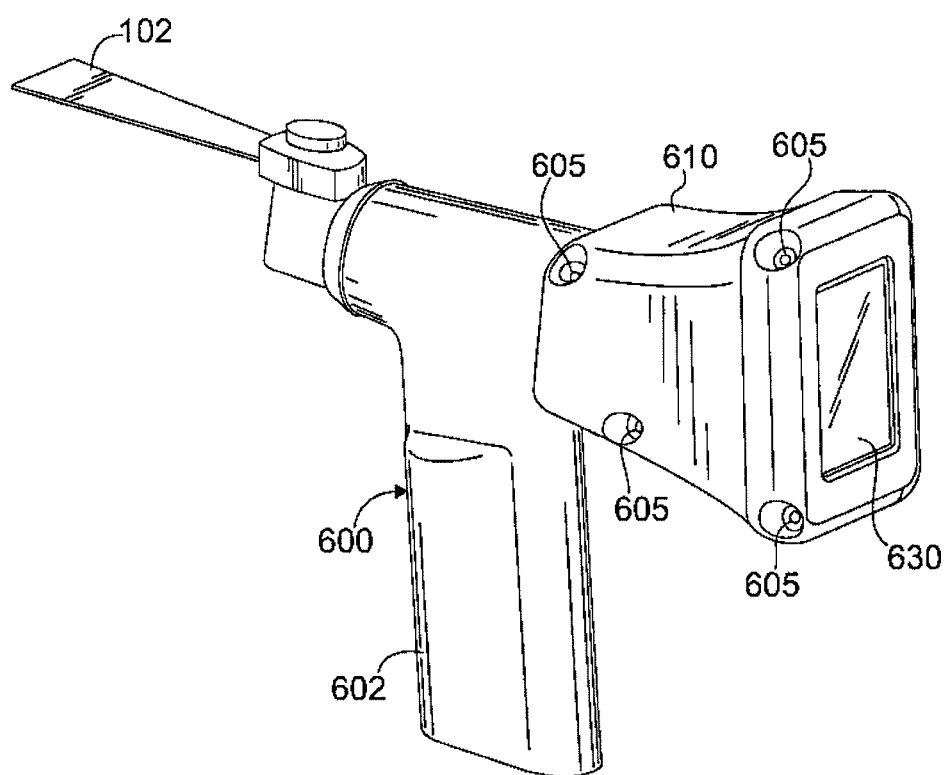
FIG. 20 is a perspective view of a surgical instrument having a housing with embedded markers and an onboard screen in line with the cutting instrument.

For instance, referring to FIG. 3 an alternate embodiment of surgical instrument 500 is illustrated along with corresponding elements for a system. The surgical instrument 500 is operable to assist in automated surgery in a surgical suite as discussed above in connection with the surgical instrument 100 described above. For instance, as described above, the system may include a tracking system 120 that operates to detect the position of the surgical instrument 500 relative to the patient. In the present instance, the position detection device detects the position of one or more markers 505 on the surgical instrument and one or more markers connected to the patient. Although the instrument illustrates the markers on a frame as with the first embodiment, the markers need not be mounted on a frame. Instead, as shown in FIG. 20, the markers 605 may be embedded in the structure of the surgical instrument 600, such as on the housing 610 away from the gripping area 602, or on the barrel or top portion of the surgical instrument. If embedded markers are utilized, the markers 605 include a portion that is readily visible to either transmit a signal or light if they are active markers, or reflect light or other signal if the markers are passive markers. In the present instance, the markers 605 are passive markers that are embedded in the surgical instrument. The markers are located on multiple positions of the instrument and on multiple faces, so that the tracking system can identify the orientation of the instrument regardless of which face of the instrument is facing the tracking system.

In addition to other aspects, the surgical instrument 500 incorporates a number of features on board the instrument itself so that the instrument can be used to perform a number of functions independent of the processing done by the OR computer 80. Additionally, the surgical instrument may incorporate wireless communication with the OR computer 80.

Referring to FIG. 3 the surgical instrument 500 includes a tool, such as a saw 510, a microcontroller 515 for monitoring and controlling operation of the tool 510, and a wireless unit 520. The instrument 500 also includes an antenna 525. The wireless unit 520 and antenna 525 allow the instrument to send data to the OR computer 80 regarding multiple status parameters, such as blade bending, saw speed and battery charge. In addition, the OR computer 80 includes a wireless unit 86, such as a bluetooth wireless element, and an antenna 87. The wireless unit 86 and antenna 87 allow the OR computer to send and receive data wirelessly to and from the surgical instrument 500.

As described previously, the OR computer 80 may be used to guide the surgeon's operation of the surgical tool during a procedure. For instance, the system may track the position of the surgical tool in real time and turn on or off the surgical tool depending on whether the tool is in proper alignment. For instance, if the system detects that the surgical tool is adjacent an area to be resected, the system may send a signal wirelessly to the tool. If the tool does not receive such a signal, the tool will not operate. Specifically, the surgical tool may have a manual switch that the surgeon can manually turn on to operate the tool. However, the tool will only run if both the manual switch is switched to the on position and if the tool also receives a signal indicating that the tool is properly positioned to perform a procedure. If either the surgeon switches the tool off or if the tool does not receive a signal indicating that the tool is properly positioned, the tool will not turn on for cutting.

As described above, the tool 500 may receive signals wirelessly to control operation of the tool. In addition to signals controlling the on/off function of the tool, signals may also be used to control other operation of the tool. For instance, the tool may receive signals that operate to control the speed of the tool. For example, as described above, the system may track the position of the tool, so that the system can track whether the tool is adjacent a cutting boundary for a desired procedure. As the tool approaches the boundary, the system may send a signal to the tool indicating that the tool should be attenuated to reduce the speed of the tool. The circuitry in the tool 500 then attenuates the operation of the tool in response to the wireless signal.

In addition to the system controlling the surgical instrument via wireless signals, the surgical instrument may control operation of the system via wireless signals For instance, the surgical tool may include various actuators, such as buttons, a joystick or a mouse ball. The operation of such actuators may be used as input signals to control operation of the OR computer. For example, operation of a joystick on the surgical tool 500 may send signals to the OR computer 80, causing the graphics displayed on the display 85 to scroll in a particular direction. Similarly, one or more buttons can be programmed to send wireless signals to change the perspective or magnification of the graphic being displayed.

Figure 16:
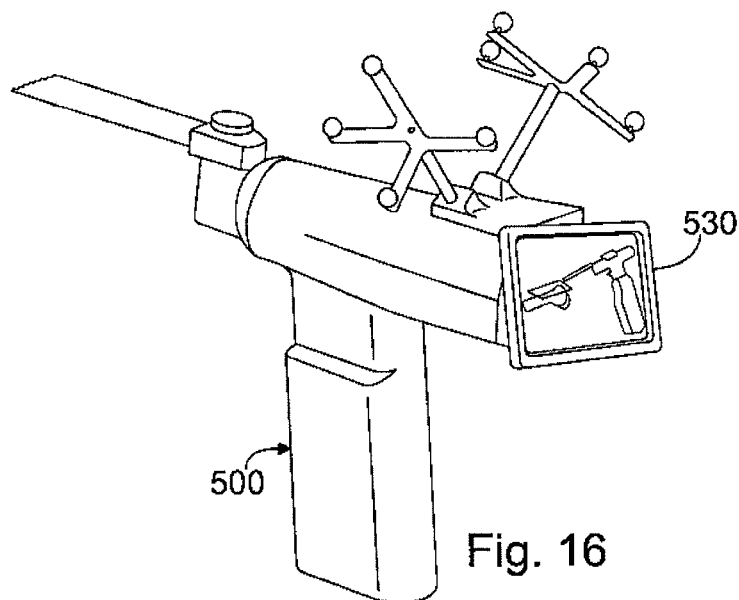
FIG. 16 is an alternative embodiment of a surgical tool operable in connection with the surgical suite of FIG. 1 or FIG. 3.
Figure 17:
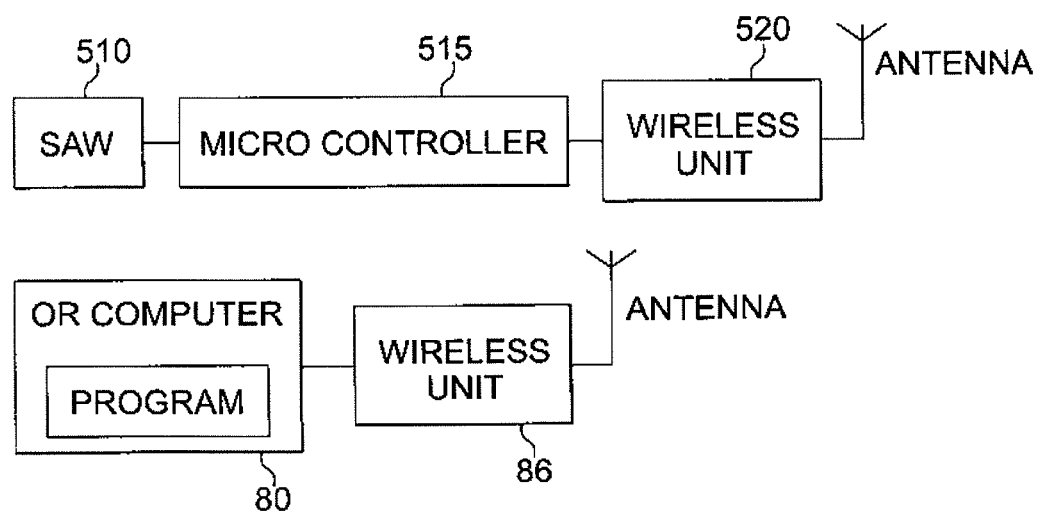
FIG. 17 is a block diagram of the wireless features of the surgical suite illustrated in FIG. 3.

In addition to including actuators, the surgical tool 500 may include a display 530 or view screen as shown in FIG. 16. Specifically, as described above, the tool may include a wireless connection for receiving data from the OR computer 80. The OR computer may transmit graphics data to the tool so that the display 530 may display the same graphics as are displayed on the main OR computer 80 display 85. Alternatively, the display 530 may display an alternate view to the graphic being displayed on the OR computer display 85. For instance, the small screen may show just a portion of the image shown on the large display 85. The small area may be automatically determined based on the area of interest in the view on the main display. Alternatively, the system may incorporate a number of pre-defined or user defined views, similar to the pre-defined views discussed above. The pre-defined views may be an entire list of views that are defined for the small screen. Additionally, as with the main display, the surgical instrument may be configured to automatically change the view based on the position and orientation of the surgical instrument, or in response to the view being shown on the main display 85. Further still, as shown in FIG. 20, the onboard screen 630 may be positioned so that it is in-line with the cutting instrument, and the small display may include one or more alignment elements on the view. For instance, the view on the onboard display that includes alignment lines or indicators that show angular alignment, such as roll, pitch etc. Still further, the onboard display may include lines such as a line showing where the surgical instrument should be located along with a line showing where the surgical instrument is actually located. Further still, the onboard screen may be a touch screen to allow input controls directly through the onboard screen. In this way, the display screen 530 may be used to guide the surgeon during a procedure in the same way that the OR computer display 85 may be used to guide the surgeon.

As previously discussed, preferably a pointer is provided for identifying reference points on the patient. Although the pointer has been described as a separate element, the pointer may be integrated into the surgical tool. For instance, since the configuration of the saw blade is known, the tip of the saw blade can operate as a pointer. Alternatively, a dedicated pointer may be incorporated onto the surgical tool. It may be desirable to configure the pointer so that it can be extended and retracted as necessary so that the pointer can be readily used, while not interfering with the operation of the cutting tool during a procedure.

The operation of the pointer element may operate in conjunction with an actuator on the surgical tool. For instance, the tool may include a button for indicating that the pointer is positioned at a reference point. When the surgeon positions the pointing element at a point to be registered, the surgeon simultaneously presses the button, sending a signal to the OR computer indicating that the point is to be registered as a reference point. The OR computer detects the position of the surgical tool as determined by the position detection device, and stores the data regarding the location of the reference point. In this way, the OR computer stores information regarding the position of the surgical tool in response to actuation of the button on the surgical tool.

It will be recognized by those skilled in the art that changes or modifications may be made to the above-described embodiments without departing from the broad inventive concepts of the invention. It should therefore be understood that this invention is not limited to the particular embodiments described herein, but is intended to include all changes and modifications that are within the scope and spirit of the invention as set forth in the claims.

What is claimed is:

1. A method for guiding a freehand surgical procedure using a freehand surgical saw, the method comprising steps of:
   creating an electronic three dimensional representation of a portion of a patient to which the guided freehand surgical procedure is to be performed;
   identifying a portion of the electronic three dimensional representation of the portion of the patient corresponding to a portion of tissue for which the guided freehand surgical procedure is to be performed to form a planar cut in the portion of the patient;
   displaying a three dimensional surgical scene that depicts an orientation of the electronic three dimensional representation of the portion of the patient and further depicts an electronic three dimensional representation of a blade of the freehand surgical saw during the guided freehand surgical procedure;
   altering an electronic representation of a boundary of the blade of the freehand surgical saw by elongating the electronic three dimensional representation of the blade along a cutting plane within the three dimensional surgical scene to aid in alignment with the orientation of the electronic three dimensional representation of the portion of the patient;
   tracking the freehand surgical saw while performing the guided freehand surgical procedure to obtain data regarding the position and orientation of the freehand surgical saw blade relative to the portion of the patient;
   varying the display of the electronic three dimensional representation of the portion of the patient and the electronic three dimensional representation of the blade in response to the position and orientation data obtained during the tracking step; and
   assessing an aspect of the planar cut.

2. The method of claim 1, wherein the step of varying the display comprises varying the orientation of the electronic three dimensional representation of the portion of the patient and the electronic three dimensional representation of the blade displayed from an automatic selection based on the location of the freehand surgical saw relative to the portion of the patient.

3. The method of claim 2, wherein the automatic selection displays a sagittal view of the portion of the patient, a lateral view of the portion of the patient, or a medial view of the portion of the patient.

4. The method of claim 1, further comprising a step of:
   tracking data for a user regarding information input into a surgical system by the user in connection with one or more surgical procedures, wherein the step of varying the display comprises the step of varying the display in response to both the data obtained during the step of tracking the tool and the data obtained during the step of tracking the data for the user.

5. The method of claim 1, further comprising a step of:
manually altering the orientation of the electronic three dimensional representation of the portion of the patient and the electronic three dimensional representation of the blade in the display on-board the freehand surgical saw during the guided freehand surgical procedure.

6. The method of claim 5, wherein the step of manually altering the orientation further comprises operating a control on the freehand surgical saw.

7. The method of claim 1, further comprising a step of:
modulating the operation of the freehand surgical saw during the step of performing the guided freehand surgical procedure.

8. The method of claim 7, wherein the step of modulating the operation of the freehand surgical saw inhibits the operation of the freehand surgical saw when the saw blade is in an improper position or an improper orientation.

9. The method of claim 7, wherein the step of modulating the operation of the freehand surgical saw permits the operation of the freehand surgical saw when the saw blade is in a proper position or a proper orientation.

10. The method of claim 1, wherein during the performing the guided freehand surgical procedure step, the displaying step adjusts to represent the electronic three dimensional representation of the blade of the freehand surgical saw moving relative to the progress of forming the planar cut in the portion of the patient.

11. The method of claim 1, wherein the displaying step further comprises altering a shape used to represent the orientation of the electronic three dimensional representation of the blade of the freehand surgical saw during the guided freehand surgical procedure, wherein the shape of the blade is altered to indicate a degree of twisting of the blade relative to the cutting plane.

12. The method of claim 11, wherein the shape used to represent the orientation of the electronic three dimensional representation of the blade of the freehand surgical saw is a line when the blade of the freehand surgical saw is aligned.

13. The method of claim 11, wherein the shape used to represent the orientation of the electronic three dimensional representation of the blade of the freehand surgical saw is rounded when the blade of the freehand surgical saw is misaligned, wherein the roundedness of the blade is altered based on a variation of an angle between the blade and the cutting plane.

14. The method of claim 1, wherein after the altering step the electronic representation of a boundary of the blade of the freehand surgical saw includes an opaque portion and a semi-transparent portion.

15. The method of claim 14, wherein the opaque portion corresponds to actual surgical saw and the semi-transparent portion corresponds to the aspect of the blade to aid in alignment.

16. The method of claim 1, wherein the assessing the aspect of the planar cut includes:
evaluating whether a surface finish of the planar cut will bond with a prosthesis;
evaluating a fit of the planar cut to the prosthesis;
evaluating an alignment of the planar cut with the prosthesis; and
evaluating an accuracy of the planar cut for engagement with the prosthesis.

17. A system for guiding a freehand surgical procedure using a freehand surgical saw, the system comprising:
means for creating an electronic three dimensional representation of a portion of a patient to which the guided freehand surgical procedure is to be performed;
means for identifying a portion of the electronic three dimensional representation of the portion of the patient corresponding to a portion of tissue for which the guided freehand surgical procedure is to be performed to form a planar cut in the portion of the patient;
means for displaying a three dimensional surgical scene that depicts an orientation of the electronic three dimensional representation of the portion of the patient and further depicts an electronic three dimensional representation of a blade of the freehand surgical saw during the guided freehand surgical procedure;
means for altering an electronic representation of a boundary of the blade of the freehand surgical saw by elongating the electronic three dimensional representation of the blade along a cutting plane within the three dimensional surgical scene to aid in alignment with the orientation of the electronic three dimensional representation of the portion of the patient;
means for tracking the freehand surgical saw while performing the guided freehand surgical procedure to obtain data regarding the position and orientation of the freehand surgical saw blade relative to the portion of the patient;
means for varying the display of the electronic three dimensional representation of the portion of the patient and the electronic three dimensional representation of the blade in response to the position and orientation data; and
means for assessing an aspect of the planar cut.

18. The system of claim 17, further comprising:
means for altering a shape used to represent the orientation of the electronic three dimensional representation of the blade of the freehand surgical saw during the guided freehand surgical procedure, wherein the shape of the blade is altered to indicate a degree of twisting of the blade relative to the cutting plane.

19. The system of claim 18, wherein the shape used to represent the orientation of the electronic three dimensional representation of the blade of the freehand surgical saw is a line when the blade of the freehand surgical saw is aligned.

20. The system of claim 18, wherein the shape used to represent the orientation of the electronic three dimensional representation of the blade of the freehand surgical saw is rounded when the blade of the freehand surgical saw is misaligned, wherein the roundedness of the blade is altered based on a variation of an angle between the blade and the cutting plane.

\* \* \* \* \*